United States Patent [19]
Weis et al.

[11] Patent Number: 5,559,101
[45] Date of Patent: Sep. 24, 1996

[54] L-RIBOFURANOSYL NUCLEOSIDES

[75] Inventors: Alexander L. Weis; Kirupathevy Shanmuganathan, both of San Antonio, Tex.; Charles T. Goodhue, Rochester, N.Y.

[73] Assignees: Genencor International, Inc., Rochester, N.Y.; Lipitek, Inc., San Antonio, Tex.

[21] Appl. No.: 328,304

[22] Filed: Oct. 24, 1994

[51] Int. Cl.$^6$ .......................... A61K 31/70; C07H 19/00
[52] U.S. Cl. ................. 514/45; 514/46; 514/49; 514/50; 536/27.14; 536/27.21; 536/27.6; 536/27.62; 536/27.8; 536/27.81; 536/28.2; 536/28.5; 536/28.53; 536/28.54; 536/28.55
[58] Field of Search ................... 536/27.14, 27.21, 536/27.6, 27.8, 27.81, 28.5, 28.53, 28.54, 28.55, 27.62, 28.2; 514/45, 46, 49, 50, 25

[56] References Cited

U.S. PATENT DOCUMENTS

| | | | |
|---|---|---|---|
| 3,457,255 | 7/1969 | Jones et al. | 536/27.22 |
| 3,817,982 | 6/1974 | Verheyden et al. | 536/27.14 |
| 4,340,729 | 7/1982 | D'Souza et al. | 536/28.55 |
| 4,659,698 | 4/1987 | Imbach et al. | 514/49 |
| 4,880,782 | 11/1989 | Eckstein et al. | 514/45 |
| 4,918,056 | 4/1990 | Bobek et al. | 514/25 |

FOREIGN PATENT DOCUMENTS

| | | |
|---|---|---|
| 24522/88 | 5/1989 | Australia. |
| 0199451A2 | 10/1986 | European Pat. Off.. |
| 0206497A2 | 12/1986 | European Pat. Off.. |
| 0261595A2 | 3/1988 | European Pat. Off.. |
| 0285884A2 | 10/1988 | European Pat. Off.. |
| 296281A5 | 11/1991 | German Dem. Rep.. |
| 1620185 | 2/1970 | Germany. |
| 1378408 | 12/1974 | United Kingdom. |
| WO88/00050 | 1/1908 | WIPO. |
| WO88/04662 | 6/1988 | WIPO. |
| WO90/01036 | 2/1990 | WIPO. |
| WO90/08147 | 7/1990 | WIPO. |
| WO92/06102 | 1/1992 | WIPO. |
| WO92/08727 | 5/1992 | WIPO. |
| WO93/03733 | 3/1993 | WIPO. |

OTHER PUBLICATIONS

H. Aoyama, Bull. Chem. Soc. Jpn., 60:2073–2077 (1987).
M. Asai, et al., Chem. Pharm. Bull., 15(12), 1863–1870 (1967).
U. Asseline, et al., Nucleic Acids Research, vol. 19, No. 15, 4067–4074 (1991).
M. V. Baud, et al., Tetrahedon Letters, vol. 31, No. 31, 4437–4440 (1990).
A. Bloch, et al., J. Chem. vol. 10, No. 5, 908–912 (1967).
G. Etzold, et al., Chem. Ber., 101:226–234 (1968).
V. Fucik, et al., Nucleic Acids Research, vol. 1, No. 4, 639–644, Apr. 1974.
S. Fujimori, et al., Nucleosides & Nucleotides, 11(2–4), 341–349 (1992).
C. Genu–Dellac, et al., Nucleosides & Nucleotides, 10(6), 1345–1376 (1991).
C. Genu–Dellac, et al., Antiviral Chem. & Chemother. 2(2), 83–92 (1991).
C. Genu–Dellac, et al., Tet. Letters, vol. 32, No. 1, 79–82 (1991).
G. Gosselin, et al., Antimicrob. Agents Chemother., vol. 38, No. 6, 1292–1297, Jun. 1994.
J. G. Gu, et al., J. Neurochemistry, vol. 56, 548–552 (1991).
A. Holy, Nucleic Acid Chemistry, Part 1, 347–353, Eds. L. B. Townsend and R. S. Tipson, Wiley & Sons, New York (1978).
A. Holy, et al., Biol. Chem. Hoppe–Seyler, 366:355–359, Apr. 1985.
A. Holy, Nucleic Acid Chemistry, vol. 2, 527–532 (1978).
A. Holy, et al., coll. Czech. Chem. Commun., vol. 34, 3383–3401 (1969).
M. Jurovcik, et al., Febs Letters, vol. 18, No. 2, 274–276 (1971).
A. M. Kritzyn, et al., Coll. Czech. Chem. Commun., vol. 40, 3211–3219 (1975).
P. Langen et al., Progress in Antimicrobial and Anticancer Chemotherapy, Proceedings of the 6th International Congress of Chemotherapy, University Park Press, England, 1970, vol. II, 394–397.
K. F. Lau, et al., Cancer Chemotherapy Reports, Part II, vol. 3, 95–109 (1972).
L. M. Lerner, Preparation of Nucleosides, vol. 34, No. 1, 101–103 (1969).
T–S Lin, et al., Biochem. Pharma., vol. 47, No. 2, 171–174 (1994).
M. Miwa, et al., Chem. Pharm. Bull., 38(4), 998–1003 (1990).
D. H. Murray, et al., J. Phar. Sci., vol. 56, No. 7, 865–870 (1967).
N. Nagasawa, et al., J. Org. Chem., 32:251–252 (1967).
C. Perigaud, et al., Nucleosides & Nucleotides, 11(2–4), 903–945 (1992).
S. Savithiry, et al., Physiol. Plant., 84:460–466 (1992).
B. Schwarz, et al., Coll. Czech. Chem. Commun. 45:3217–3230 (1980).
B. Shimizu, et al., Chem. Pharm. Bull., 15(12):2011–2014 (1967).
B. Shimizu, et al., Nucleic Acid Chemistry, vol. 2, 783–792 (1978).
S. Spadari, J. Med. Chem., 35:4214–4220 (1992).
R. A. Taube, et al., Biochimica et Biophysica Acta, 255:6–18 (1972).
I. Votruba, et al., Febs Letters, vol. 19, No. 2, 136–138 (1971).
M. A. Waqar, et al., J. Cell. Physiol., 121:402–408 (1984).
A. F. Wu, et al., Biochemistry, 63:1222–1226 (1969).

*Primary Examiner*—James O. Wilson
*Attorney, Agent, or Firm*—Margaret A. Horn

[57] ABSTRACT

This invention relates to α and β L-ribofuranosyl nucleosides, processes for their preparation, pharmaceutical compositions containing them, and methods of using them to treat various diseases in mammals.

13 Claims, No Drawings

L-RIBOFURANOSYL NUCLEOSIDES

FIELD OF THE INVENTION

This invention relates to L-ribofuranosyl nucleosides and intermediate or derivatives thereof useful in the synthesis of such nucleosides, processes for their preparation, pharmaceutical compositions containing such, and methods of using such compounds to treat various diseases, particularly cancer, in mammals.

BACKGROUND OF THE INVENTION

Perigaud, C., et al, *Nucleosides and Nucleotides*, 11(2–4), 903–945 (1992), provide a useful overview of the current state of the art relating to the use of nucleosides and/or nucleotides as chemotherapeutic agents (including use as anticancer, antiviral and antibacterial agents). As described in this review article, the term "nucleoside(s)" relates to naturally-occurring nucleosides which are distinguished depending on the base, for example, adenine and guanine (A and G, respectively) have a purine base, whereas cytosine, uracil, thymine and hypoxanthine (C, U, T and H, respectively) have a pyrimidine base.

Nagasawa, N., et al., *J. Org. Chem.*, 32, 251–252 (1967), describe the production of certain D-ribopyranosyl nucleosides (particularly 9-(2'-Deoxy-β-D-ribopyranosyl) adenosine).

Fucik, V., et al., *Nucleic Acids Research*, Vol. 1, No. 4 (1974) 639–644, describe structural effects of chemical modification upon the affinity of purine nucleosides to cytidine-transport system in *Bacillus subtilis* using a series of modified derivatives including certain ribopyranosyl nucleosides.

Baud, M. V., et al., *Tetrahedron Letters*, Vol. 31, No. 31, pp. 4437–4440 (1990), describes the synthesis of certain 2'-deoxyribonucleoside compounds starting from available sugars (2-deoxyribofuranosyl or pyranosyl). The compounds described in this paper are all D-isomers.

Spadari, S., et al, *J. Med. Chem*, 35, pp. 4214–4220 (1992), describes certain L-β-nucleosides useful for treating viral infections including Herpes Simples Virus Type I.

Holy, A., *Nucleic Acid Chemistry*, Vol. 1, 347–353 (1978), describes the synthesis of 2'-deoxy-L-uridine.

WO 92/08727 describes certain 2'-L-desoxyuridines and their use for treating viruses.

As is well known, sugars found in natural nucleic acids are D-ribose and D-deoxyribose in almost all cases. Much research has been done to investigate the chemical, and biological activities of the D-isomers of ribonucleotides and ribonucleosides, however, far less work has been done with the L-isomers. This is primarily due to the fact that the synthesis of the L-isomers is much more difficult, often involving the optical resolution of the D,L-isomers of nucleosides with the aid of microorganisms and enzymes. (See generally, Asai, M., et al., *Chem. Pharm. Bull.*, 15(12), 1863–1870 (1967).) The known activity of D-nucleoside compounds, and the successful commercialization of several of such D-sugar-nucleoside compounds, (see Perigaud, C., et al., supra, for a discussion of D-nucleoside analogs which have gained commercial acceptance) led in-part to the present work relating to the L-isomers of certain nucleoside analogs.

Perhaps the best known commercial nucleobase analog is 5-fluorouracil (5-FU) the structure of which is shown below:

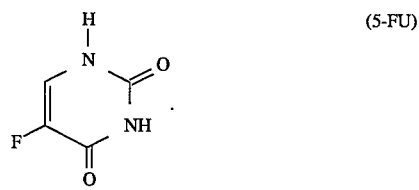

5-FU is commercially available from Roche and is one of the most commonly used drugs for treating certain types of cancer. The high acceptance of this drug is due in part to its extreme cytotoxic effects. However, it also has a narrow margin of safety and is, therefore, associated with many serious side effects including, for example, nausea, vomiting, diarrhea, alopecia, leukopenia, thrombocytopenia, etc. Additionally, 5-FU is primarily used in an intravenous formulation.

5-FU is currently dosed at short intervals due to the damage it does to normal cells. The patient is taken off chemotherapy for a time to allow recovery from the cytotoxic effects of the treatment. It is contemplated that if a drug is developed that is less cytotoxic to healthy cells it would no longer be necessary to treat the patient in periodic intervals, which may be associated with the development of multiple drug resistance often exhibited in treated cancer cells. Specifically, as a tumor is being killed the cells that are most resistant to the drug die slower and, therefore, when the treatment is stopped (often because of the toxicity to normal cells) the more resistant tumor cells are left to multiply.

A significant commercial nucleoside analog is azidothymidine (AZT), commercially available as Retrovir from Burroughs Wellcome. AZT, a β-D-deoxy-ribofuranosyl derivative of the formula:

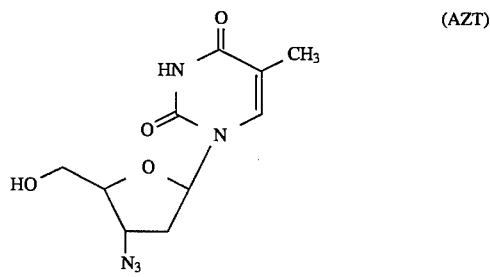

is useful as an antiviral agent, particularly against the virus responsible for the Acquired Immune Deficiency Syndrome (AIDS).

This compound, like 5-FU, is associated with a number of undesirable side effects including hematologic toxicity such as granulocytopenia and/or severe anemia.

Without intending to be limited, applicants believe that the L-nucleoside compounds as claimed in the present invention may be beneficial over compounds such as 5-FU and AZT since it is believed that L-nucleosides (as claimed) exhibit selective permeability to compromised cells. By compromised cells we mean cells such as cancer cells or other infected cells, whether the infection is bacterial, fungal, viral or parasitic. It is believed that the L-nucleosides of the present invention may be transported into or permeate these compromised cells, whereas in normal cells the L-nucleosides would not permeate. (See for example, Lin, T. S., et al., Abstract entitled "Synthesis and Biological Evaluation of 2',3'-Dideoxy-L-Pyrimidine Nucleosides as Potential Antiviral Agents against HIV and HBV", published *J. Med. Chem.*, 37 (1994) 798–803; and Spadari, S., et al., *J.*

*Med. Chem.*, 35 (1992) 4214–4220.) Therefore, to the extent these L-nucleosides are selective for compromised cells, they are less harmful to normal cells than compounds like 5-FU.

In addition to this concept of selective permeability, in viral-infected cells where therapeutic compounds often have an inhibitory mechanism related to the RNA of the cell, it is contemplated that the enzymes of such viral-infected cells may be less specific than in a normal cell and, therefore, if you can permeate the cell with an L-nucleoside, a more primitive enzyme such as an organic phosphorylases, kinases or thymidilate synthase may recognize the compound in such a way as to cause inhibition.

Therefore, although certain nucleoside analogs and/or nucleobase analogs have been commercialized for indications such as cancer and/or AIDs treatment, there is a need for a nucleoside analog which is perhaps as cytotoxic as 5-FU or is less cytotoxic but more specific than 5-FU for cancer therapy and/or a compound which is more effective and/or better tolerated than AZT for treatment of viruses.

The present invention relates to a novel group of such L-ribofuranosyl nucleosides which have interesting activity as anticancer, antiviral, antiparasitic, antifungal, antibacterial and/or antimicrobial agents. These compounds are generally water soluble, which suggests that oral deliver may be achieved, and the activity of these compounds may be more selective for compromised cells as compared to normal cells.

DETAILED DESCRIPTION OF THE INVENTION

There is provided by this invention ribofuranosyl nucleoside compounds having the formula (I):

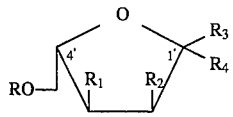

(I)

or a pharmaceutically acceptable salt thereof, wherein:

B is a naturally-occurring nucleobase (A, G, C, U, hypoxanthine or T) or a modified base comprising one or more substitutions selected from the group consisting of H, halogen, C1-C6 alkyl, C2-C6 alkenyl, C1-C6 alkoxy, C3-C6 cycloalkyl-C1-C6 alkoxy, C3-C8 cycloalkyloxy, C3-C8 cycloalkylthio, C1-C6 alkylthio, a substituted amino group, an aryl, aralkyl, aryloxy, aralkoxy, arylthio, aralkylthio, a heterocyclic ring and an amino group, provided that when the base is a pyrimidine, the atom at position 4 in the base can be sulfur, and that when the base is a purine, the atom at position 6 in the base may be sulfur;

R is H, $COR_5$, $P(O)_nR_6R_7$ or $SO_3H$ (wherein $R_5$ is alkyl of 1–5 carbon atoms or an aromatic ring structure, $R_6$ and $R_7$ are each H or alkyl of 1–5 carbon atoms and n is 2 or 3);

$R_1$ and $R_2$ are independently H, halogen, mono- or di-difluro, $OR_8$ or B (wherein $R_8$ is H, $COR_9$, $P(O)_mR_{10}R_{11}$ (wherein $R_9$ is $H_2$, substituted or unsubstituted alkyl of 1–5 carbon atoms or a substituted or unsubstituted aromatic ring structure, $R_{10}$ and $R_{11}$ are each H or alkyl of 1–5 carbon atoms and m is 2 or 3)), provided that when $R_2$ is OH, $R_2$ and B can combine to form a 5-membered cyclic ring structure;

$R_3$ and $R_4$ are independently B, H or $OR_{12}$ (where $R_{12}$ is H, $COR_{13}$, $P(O)_pR_{14}R_{15}$ (wherein $R_{13}$ is substituted or unsubstituted alkyl of 1–5 carbon atoms or a substituted or unsubstituted aromatic ring structure, $R_{14}$ and $R_{15}$ are each H or alkyl of C1-C5 carbon atoms and p is 2 or 3)), provided that:

only one of $R_1$-$R_4$ can be B;

when R=H, $R_1$=OH, $R_2$=H, $R_3$=H and $R_4$=B, then B cannot be U, C, T, 5-FU, hypoxanthine, A, or G;

when R=H, $R_1$=OH, $R_2$=OH, $R_3$=B and $R_4$=H, then B cannot be C;

when R=H, $R_1$=OH, $R_2$=OH, $R_3$=H and $R_4$=B, then B cannot be 5-FU, C, U, A or hypoxanthine;

when R=H, $R_1$=OH, $R_2$=H, $R_3$=B and $R_4$=H, then B cannot be 5-FU, A, C, G, T, U or hypoxanthine;

when R=H, $R_1$=H, $R_2$=H, $R_3$=B and $R_4$=H, then B cannot be A, C, G, T, U, 5-FU, or hypoxanthine; and when R=H, $R_1$=H, $R_2$=H, $R_3$=H and $R_4$=B, then B cannot be A, C, G, T, U, 5-FU or hypoxanthine.

Preferred compounds of the present invention include those compounds of formula (I) wherein:

$R_3$ or $R_4$ is B and the other is H, such that when $R_3$ is B the series is α and when $R_4$ is B, the series is β;

B is C, T, U, G, I, A, 5-fluorouracil, 6-thioguanine or 4-thiouracil;

R is H; and $R_1$-$R_2$ are each H or OH, or when $R_2$ is OH, $R_2$ and B combine to form a five-membered cyclic ring.

Specifically preferred compounds of the present invention are the following: α-L-ribofuranosyluracil; 1-(2,3,5-tri-O-benzoyl-α-L-ribofuranosyl)-4-thiouracil; α-L-ribofuranosyl-4-thiouracil; 1-(3,5-di-O-benzoyl-2-deoxy-β-L-ribofuranosyl)-4-thiouracil; 2'-β-L-deoxyribofuranosyl-4-thiouracil; α-L-ribofuranosyl-5-fluorouracil; β-L-ribofuranosyl guanine; β-L-ribofuranosyl-6-thioguanine and pharmaceutically acceptable salts thereof.

Also provided by this invention are processes for the preparation of the compounds of formula (I), pharmaceutical compositions containing the compounds of formula (I) and methods of using the compounds of formula (I) for the treatment of cancer in a mammal, as well as methods of using the compounds of formula (I) as antivirals, antiparasitics, antibacterials, antifungals and antimicrobial agents in a mammal.

Synthesis

The present invention describes a series of L-ribofuranosyl nucleosides useful for treating various diseases (including cancer and certain viruses). Compounds of this invention may be orally active based on their water solubility.

The compounds of this invention wherein the nucleoside has a pyrimidine base (U, T, C or substituted pyrimidine base) which is linked to the ribofuranosyl sugar via β linkage (B is $R_4$ in a compound of Formula (I)) can be made by the general Scheme I.

SCHEME I

General procedure to make β-L-ribofuranosyl pyrimidines:

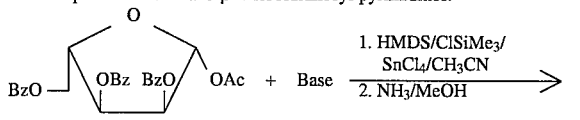

To a mixture of 1-O-acetyl-2,3,5-tri-O-benzoyl-β-L-ribofuranose (1 mol) and pyrimidine base (1 mol) in anhydrous MeCN are successively added HMDS (1 mol), ClSiMe₃ (0.8 mol) and SnCl₄ (1.2 mol). The resulting clear solution is refluxed for 1 hour when TLC indicates completion of the reaction. The solvent is evaporated and the residue dissolved in EtOAc, washed with NaHCO₃ and H₂O. The EtOAc layer is dried, filtered and evaporated to give the crude product, which is either crystallized or purified on a silica gel column to obtain the pure 2,3,5-tri-O-benzoyl-β-L-ribofuranosyl pyrimidine compounds. These compounds are stirred with NH₃/MeOH to give pure β-L-ribofuranosyl pyrimidines after purification and crystallization.

A more detailed schematic for β-linked pyrimidine compounds within the scope of the present invention is Shown in Scheme I-A.

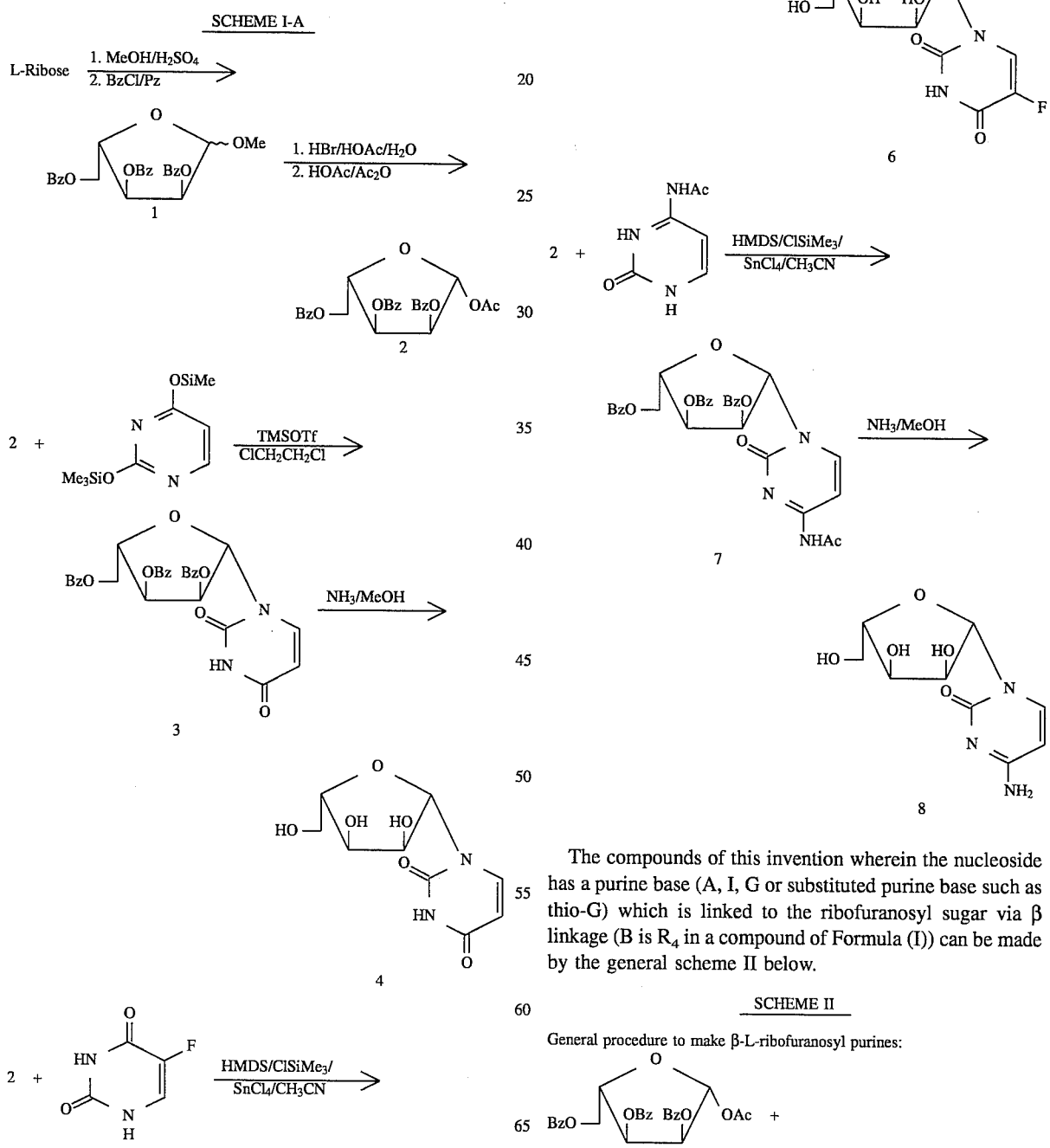

The compounds of this invention wherein the nucleoside has a purine base (A, I, G or substituted purine base such as thio-G) which is linked to the ribofuranosyl sugar via β linkage (B is R₄ in a compound of Formula (I)) can be made by the general scheme II below.

SCHEME II

General procedure to make β-L-ribofuranosyl purines:

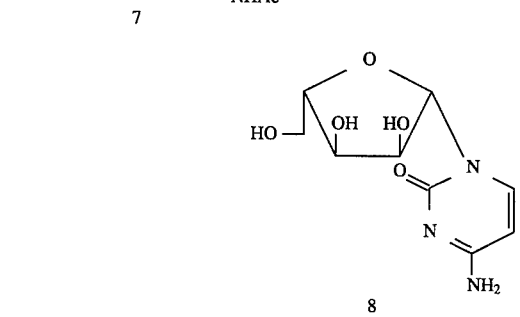

-continued
SCHEME II

Silylated Base  →  1. TMSOTf/ClCH₂CH₂Cl  2. NH₃/MeOH

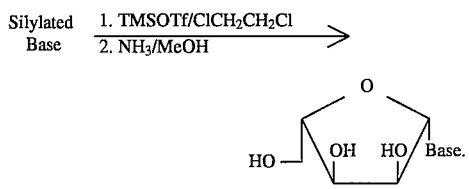

A mixture of purine base (2 mol) and (NH$_4$)$_2$SO$_4$ (catalytic amount) in HMDS is refluxed until the solution becomes clear. The resulting clear solution is concentrated to yield silylated base to which anhydrous dichloroethane is added and the solution is cooled to 0° C. Under nitrogen atmosphere a solution of 1-O-acetyl-2,3,5-tri-O-benzoyl-β-L-ribofuranose in dichloroethane (1 mol) and TMSOTf (2.1 mol) are added to the above solution and stirred at room temperature for 16 hours. The reaction is quenched with saturated NaHCO$_3$ solution and the solvent is evaporated. The residue is dissolved in EtOAc, washed with water and brine. After drying and evaporating the solvent, the residue obtained is separated on a silica gel column to give pure 2,3,5-tri-O-benzoyl-β-L-ribofuranosyl purines, which after stirring with NH$_3$/MeOH and usual purification give pure β-L-ribofuranosyl purines.

A more detailed schematic for the synthesis of β-linked purine compounds within the scope of the present invention is provided in Scheme II-A.

SCHEME II-A

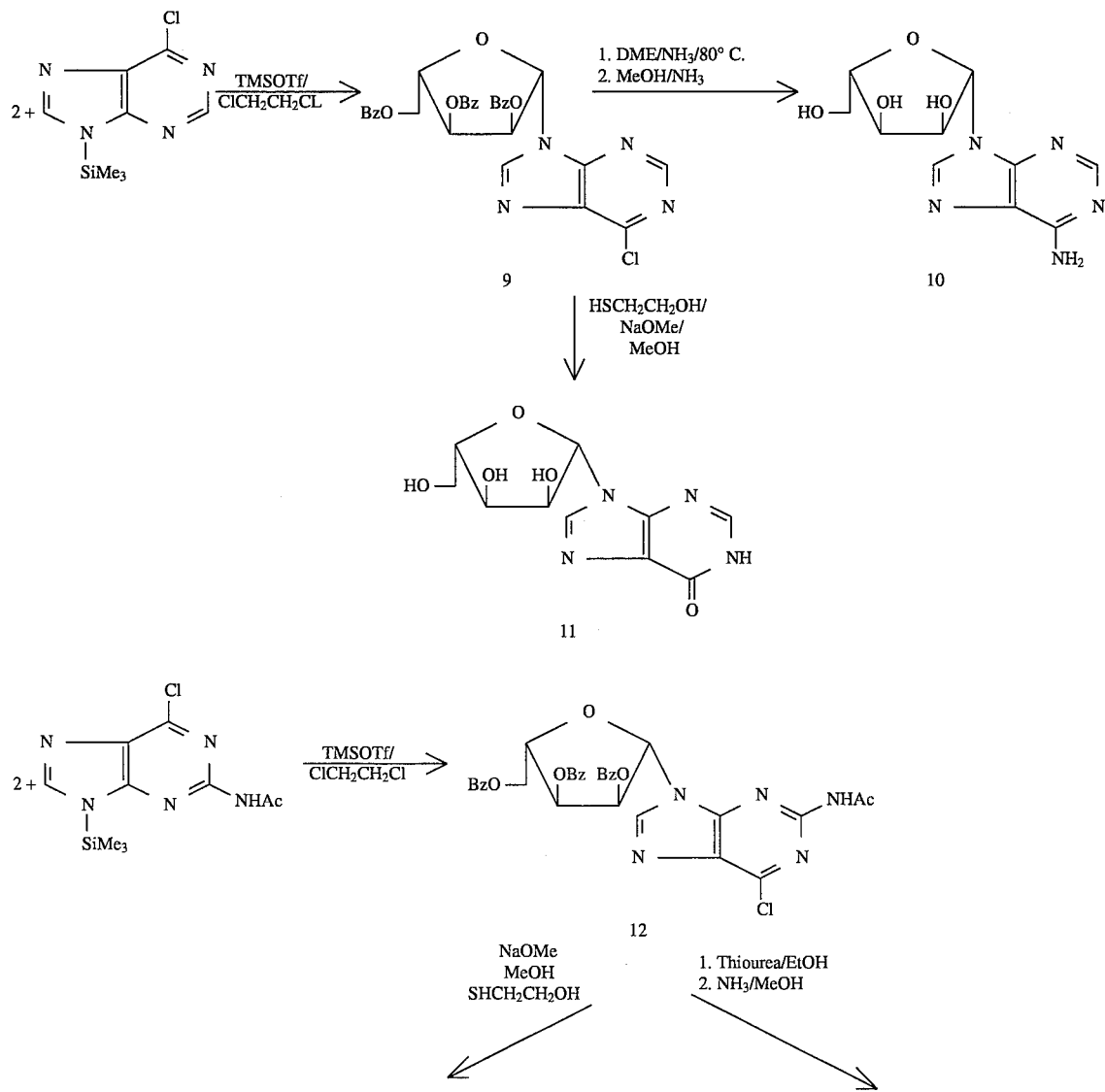

-continued
SCHEME II-A

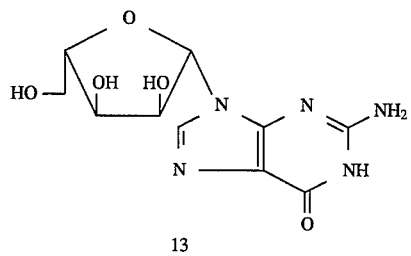

13

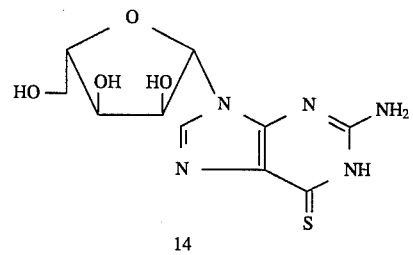

14

The compounds of this invention wherein the nucleoside has a pyrimidine base (U, T, C or substituted pyrimidine base such as 5-FU or thio-U) which is linked to the ribofuranosyl sugar via α linkage (B is $R_3$ in a compound of Formula (I)) can be made by the general Scheme III below.

SCHEME III

General procedure to make α-L-ribofuranosyl pyrimidines:

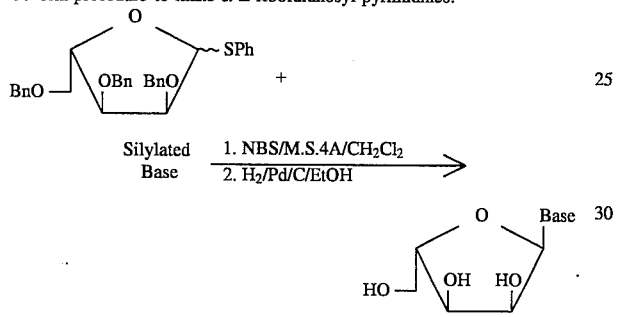

A mixture of pyrimidine base (2 mol) in HMDS and ammonium sulfate (catalytic amount) is refluxed until the solution becomes clear. The resulting clear solution is concentrated in vacuo to yield silylated base. To this silylated base in anhydrous $CH_2Cl_2$ under nitrogen atmosphere, 1-thio-2,3,5-tri-O-benzyl-L-ribofuranoside (2 mol), 4 Å molecular sieves and NBS (1.1 mol) are added. The reaction mixture is stirred at room temperature overnight and quenched with addition of $Na_2S_2O_3$ solution. The organic layer is washed with water brine and dried over $Na_2SO_4$. Evaporation of the solvent gives the crude product which is purified on a silica gel column to obtain pure 2,3,5-tri-O-benzyl-α-L-ribofuranosyl pyrimidines. These compounds are subjected to $H_2$/Pd/C reduction, followed by purification and crystallization to give pure α-L-ribofuranosyl pyrimidines.

A more detailed schematic for the synthesis of α-linked pyrimidines within the scope of the present invention is provided in Scheme III-A.

SCHEME III-A

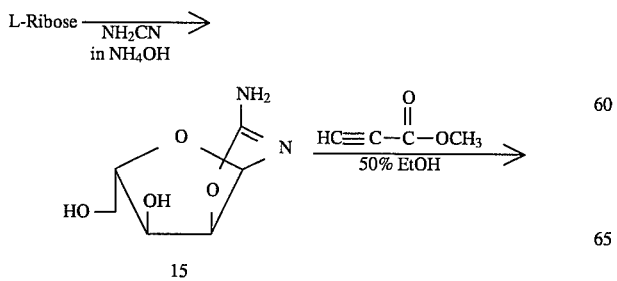

15

-continued
SCHEME III-A

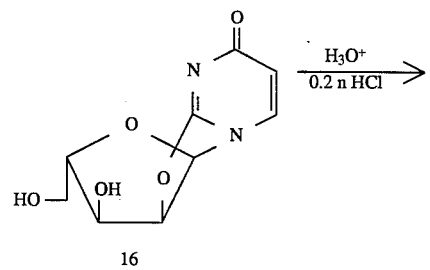

16

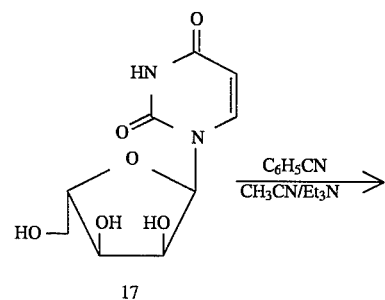

17

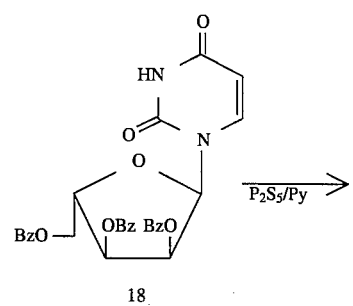

18

11
-continued
SCHEME III-A

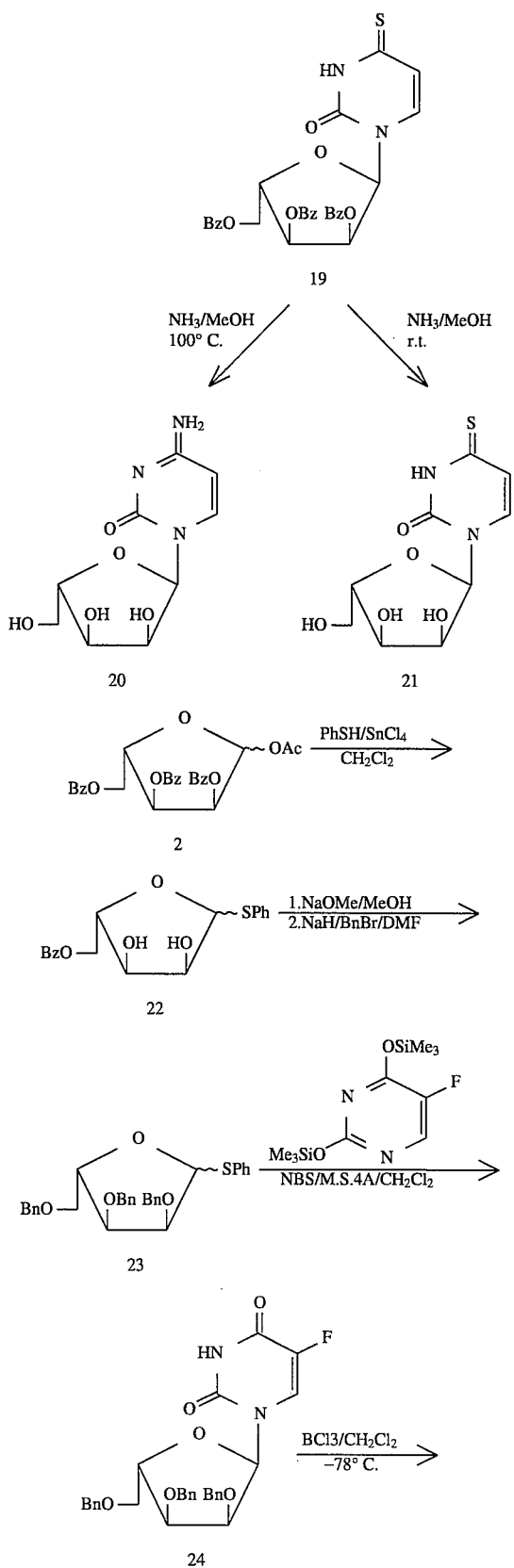

12
-continued
SCHEME III-A

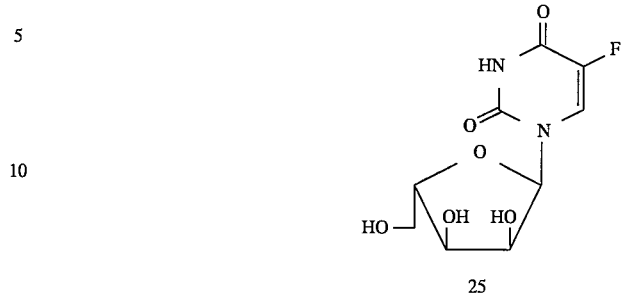

The compounds of this invention wherein the nucleoside has a purine base which is linked to the ribofuranosyl sugar via β linkage (B is $R_3$ in a compound of formula (I)) and only one of $R_1$ or $R_2$ is OH, or where $R_2$ is OH and combines with B to form a cyclic ring structure, can be made by the General Scheme IV below.

SCHEME IV

General procedeure to make β-L-2'-Deoxyribofuranosyl purines:

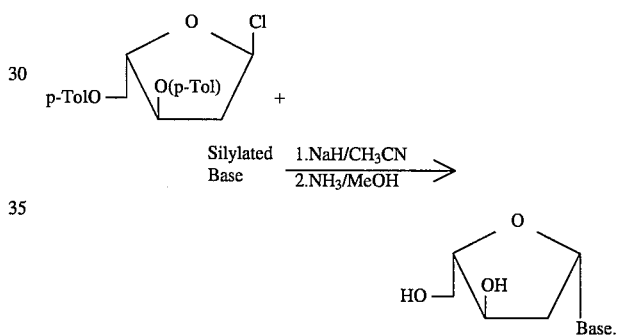

A mixture of purine base (2 mol) and NaH (2.2 mol) is stirred in anhydrous $CH_3CN$ under nitrogen atmosphere at room temperature for 30 min. 1-Chloro-2-deoxy-3,5-di-O-p-toluoyl-α-L-pentofuranose is added to the reaction mixture and stirred for 2 hours. The reaction mixture is diluted with $CHCl_3$ and filtered through Celite®. The filtrate is concentrated, redissolved in EtOAc and washed with water and brine. After drying and evaporating the solvent, the residue obtained is purified on a silica gel column to give pure 2'-deoxy- 3,5-di-O-p-toluoyl-β-L-ribofuranosyl purines. These compounds are treated with $NH_3/MeOH$ and then purified and crystallized to give pure β-L-2'-deoxyribofuranosyl purines.

A detailed schematic for similar β-linked deoxy-ribofuranosyl having pyrimidine bases is shown in Scheme IV-A.

SCHEME IV-A
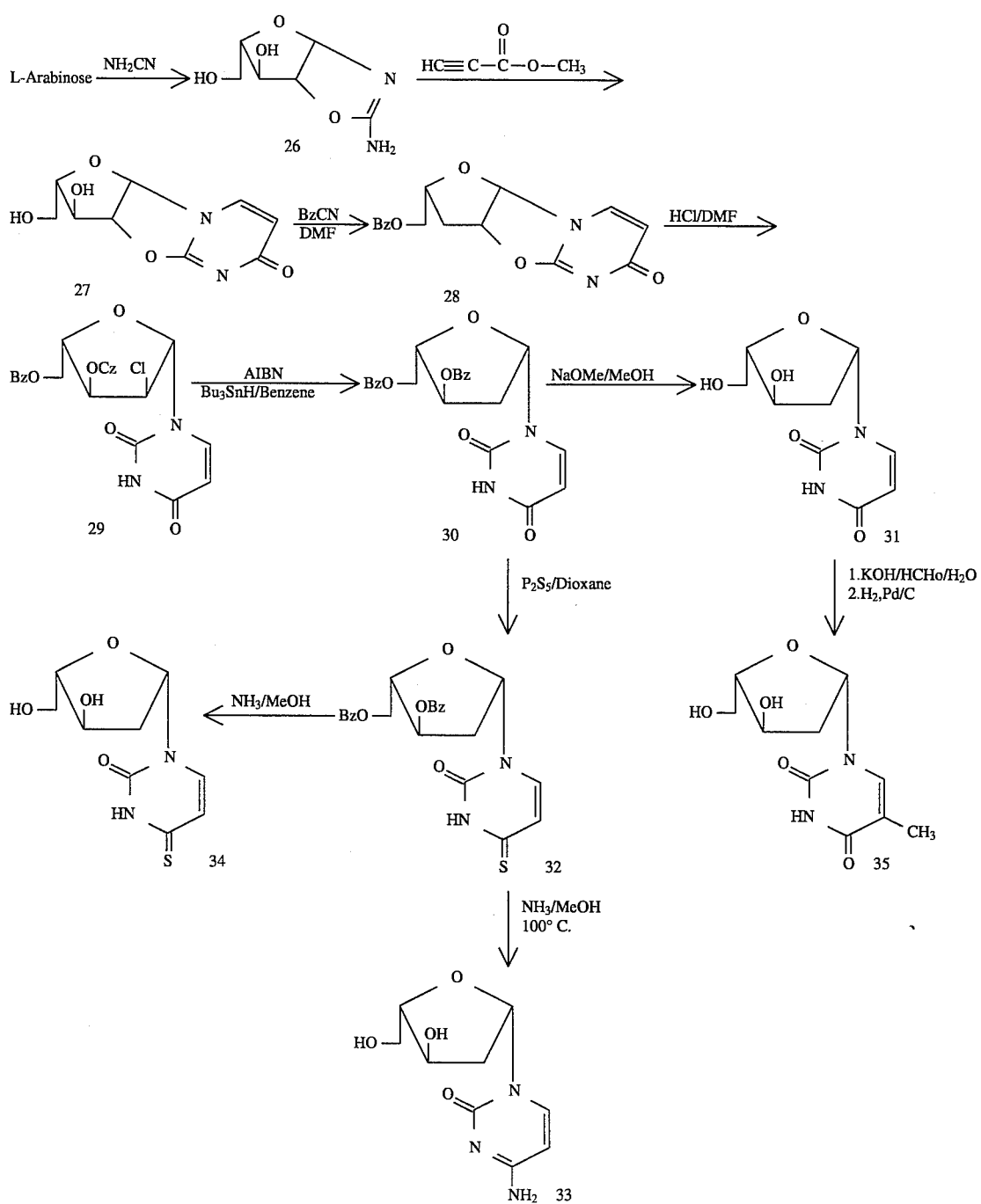
The compounds of this invention comprising α-L-2'deoxy ribofuranosyl pyrimidines and purines (including 5-FU analogs of such) are shown in Scheme V, whereas Scheme V-A shows methods for making β-linked L-2'-deoxy-ribofuranosyl compounds.
SCHEME V
General procedure to make α-L-2'-doexyribofuranosyl pyrimidines and purines:
-continued
SCHEME V
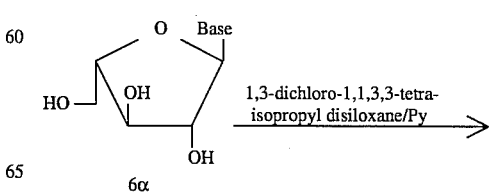

-continued
SCHEME V

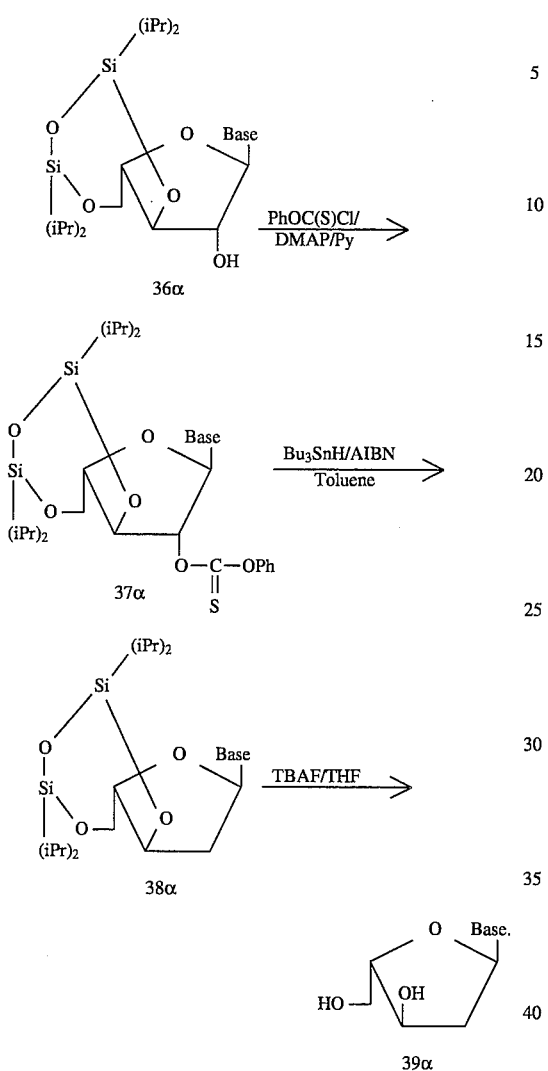

1-[3',5'-O-(1,1,3,3-Tetraisopropyldisiloxane-1,3-diyl)-α-L-arabinofuranosyl]-purine or pyrimidine (36 α)

To a stirred suspension of (6 α) (1 mol) in pyridine is added 1,3 -dichloro-1,1,3,3-tetraisopropyldisiloxane (1.2 mol). This is stirred at room temperature until the completion of the reaction (five hours), the solvent is evaporated and the residue is dissolved in EtOAc and washed with water, 5% HCl, water, saturated aqueous NaHCO₃ and brine. After drying over anhydrous Na₂SO₄ it was filtered and evaporated to give the crude product (36 α) which is used in the next step without further purification.

1-[2'-O-Phenoxythiocarbonyl-3',5'-O-(1,1,3,3-tetraisopropyl disiloxane-1,3-diyl)-α-L-arabinofuranolsyl]-purine or pyrimidine (37 α)

To a solution of (36 α) (1 mol) in anhydrous CH₃CN is added 4-dimethly amino pyridine (DMAP) (1.9 mol) and phenyl chlorothionoformate (1.1 mol). The solution is stirred at room temperature for 24 hours. Then the solvent is evaporated and the residue dissolved in EtOAc and washed with water, 5% HCl, water, saturated aqueous NaHCO₃ and brine. The EtOAc layer is dried (Na₂SO₄), filtered and evaporated. The residue is purified on a silica gel column to give pure (37 α).

3',5'-O-(1,1,3 3-Tetraisopropyldisiloxane-1,3-diyl)-α-L-purine or pyrimidine (38 α)

To a mixture of (37 α) (1 mol), AIBN (0.2 mol) in dry toluene is added Bu₃SnH (5 mol). The solution is deoxygenated with oxygen-free Ar then heated at 75° C. for four hours. The solvent is then evaporated and the residue is purified on a silica gel column to yield pure (38 α).

2'-Deoxy-α-L-purine or pyrimidine (39 α)

A mixture of (38 α) (1 mol) and TBAF (2 mol) in THF is stirred at room temperature. After completion of the reaction the solvent is evaporated and the residue is dissolved in water and washed with ether. The water is evaporated and the residue purified on a silica gel column to give pure 2'-Deoxy-α-L-purine or pyrimidine.

SCHEME V

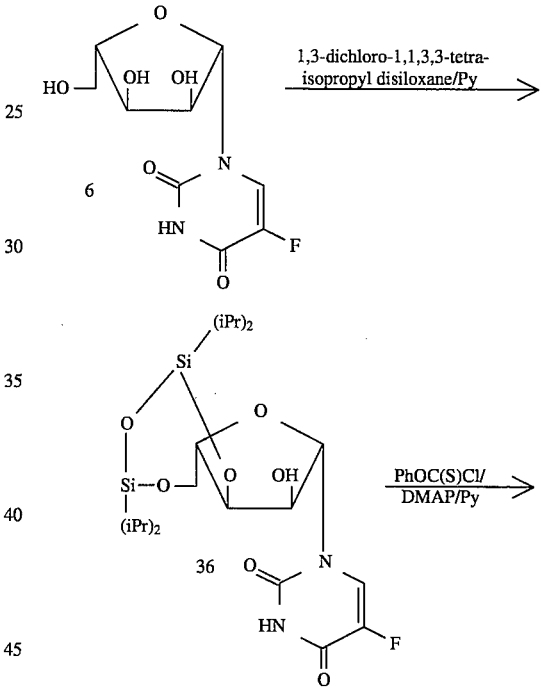

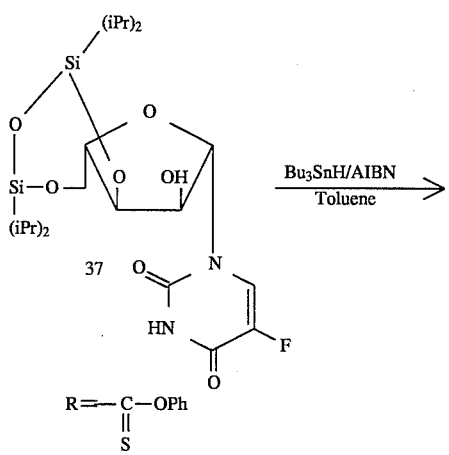

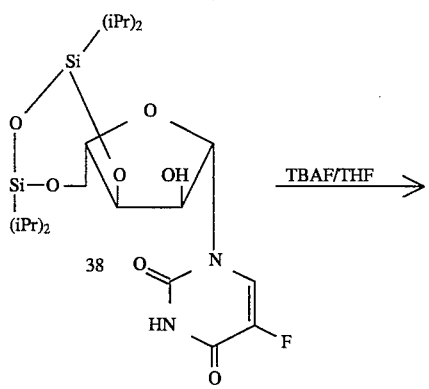

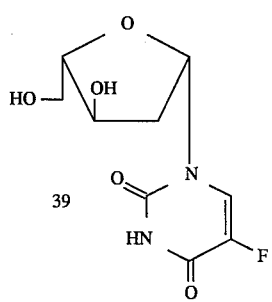

A general schematic for the synthesis of α and β-L-2'-3'-dideoxyribofuranosyl pyrimidines and purines is provided below in Scheme VI. Detailed schematics for β-linked 2'3' dideoxy pyrimidines and β-linked 2'deoxyinosine are shown in Schemes VI-A and VII.

SCHEME V

General procedure to make α and β-L-2',3'-dideoxyribofuranosyl pyrimidines and purines:

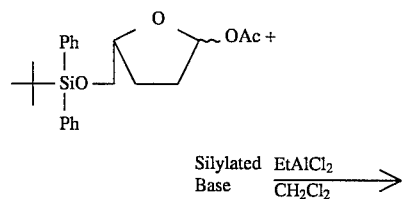

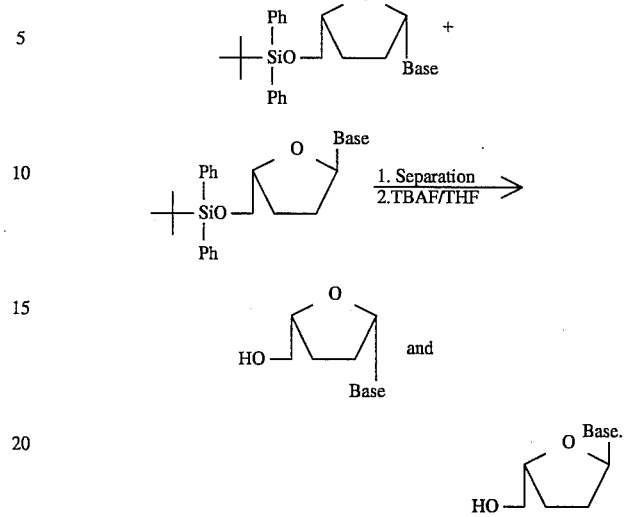

A mixture of purine or pyrimidine base (1 mol) in HMDS and ammonium sulfate (catalytic amount) is refluxed until the solution becomes clear. The resulting clear solution is concentrated in vacuo to yield silylated base. To a solution of this silylated base in anhydrous $CH_2Cl_2$ under nitrogen atmosphere, a solution of 1-O-acetyl- 5-O-(tert-butyldiphenylsilyl)-2,3-dideoxy-L-ribofurnose is added followed by the addition of $EtAlCl_2$. The reaction mixture is stirred at room temperature for an hour and then poured into an ice cold mixture of $CH_2Cl_2$ and saturated $NaHCO_3$ solution. The mixture is stirred for 10 min and filtered through Celite®. The organic layer is washed with saturated $NaHCO_3$ solution and brine. After evaporating the solvent, the α,β crude product is separated on a silica gel column to give pure α and β-5'-O-(tert-butyldiphenylsilyl)- 2',3'-dideoxy purines and pyrimidines. These compounds are treated with TBAF to remove the silyl protection, and then purified on a silica gel column to give pure α and β-dideoxy purines and pyrimidines.

The compounds of this invention wherein the nucleoside has a pyrimidine base (U, T, C or substituted pyrimidine base) which is linked to the ribofuranosyl sugar via β linkage (B is $R_3$ in a compound of formula (I)) and are 2',3'-dideoxy compounds, can be made by the general Scheme VI-A below.

SCHEME VI-A

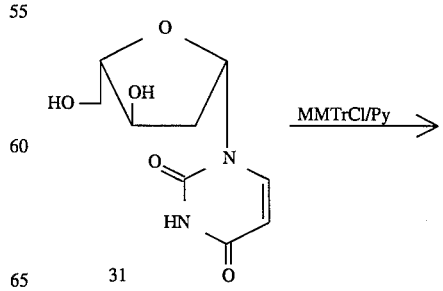

19
-continued
SCHEME VI-A
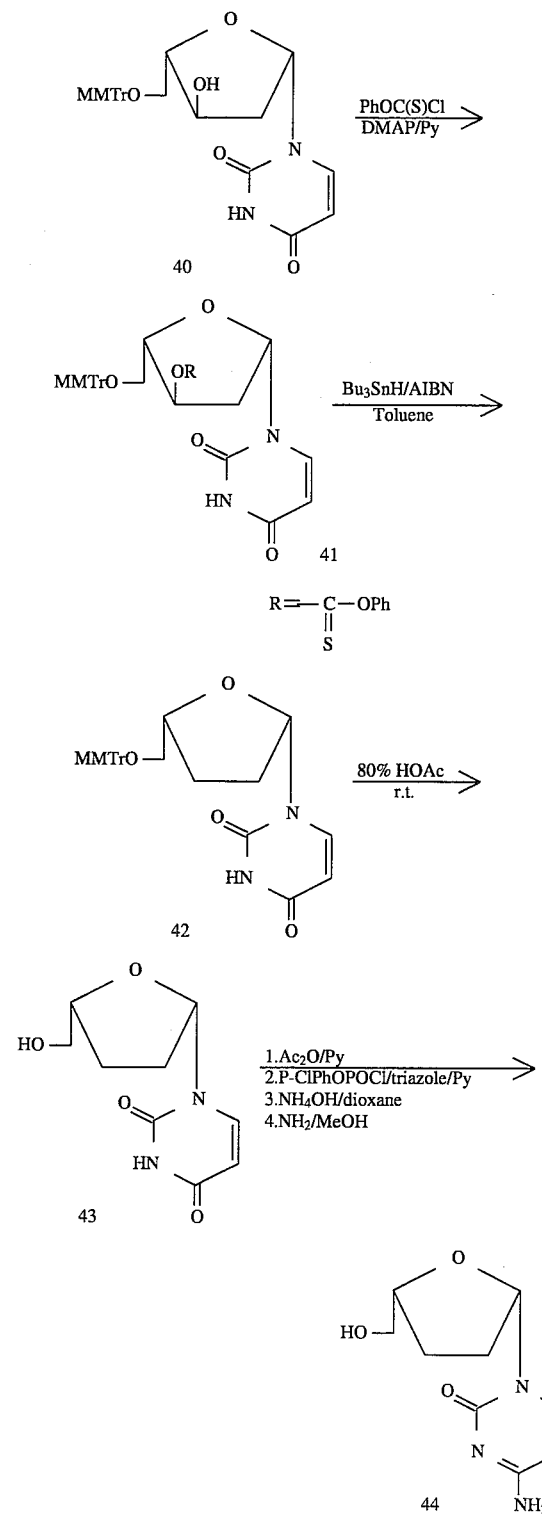
20
-continued
SCHEME VI-A
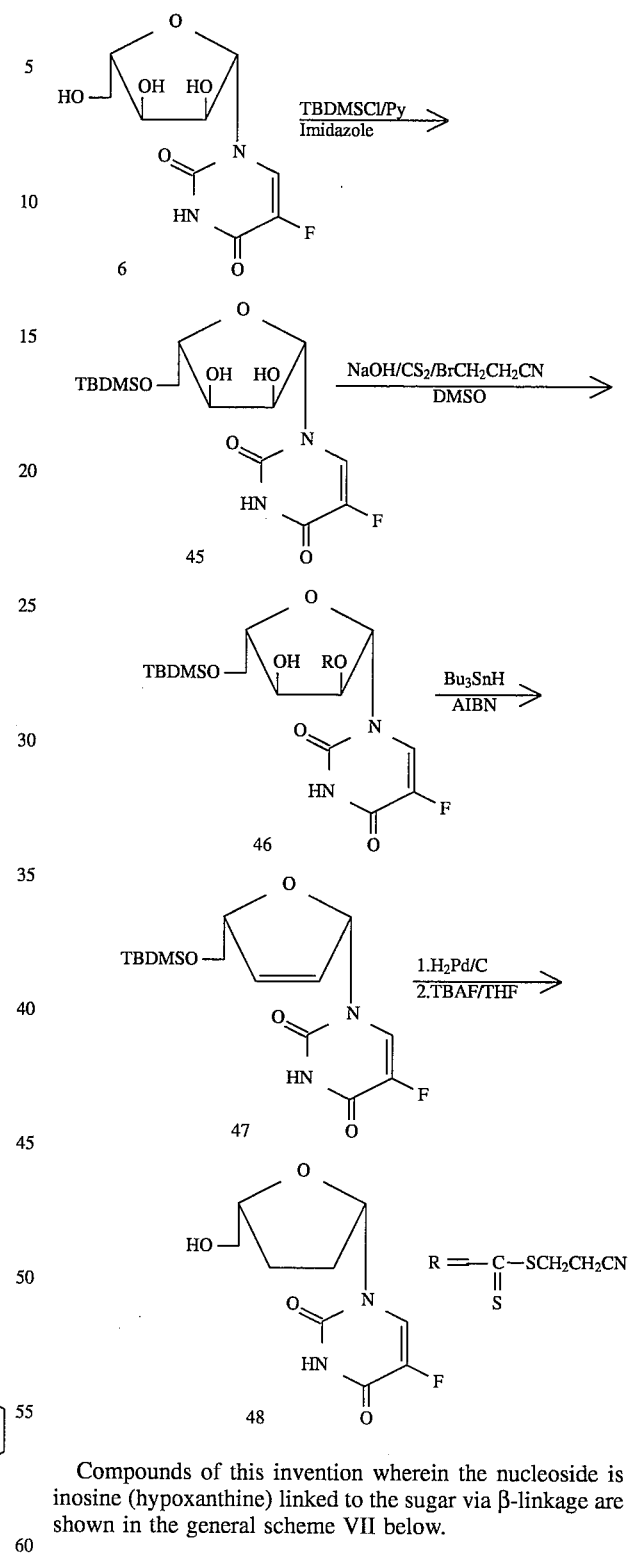
Compounds of this invention wherein the nucleoside is inosine (hypoxanthine) linked to the sugar via β-linkage are shown in the general scheme VII below.
SCHEME VII
β-L-2'-Deoxyinosine
L-Arabinose $\xrightarrow{\text{BnOH/HCl}}$

21
-continued
SCHEME VII

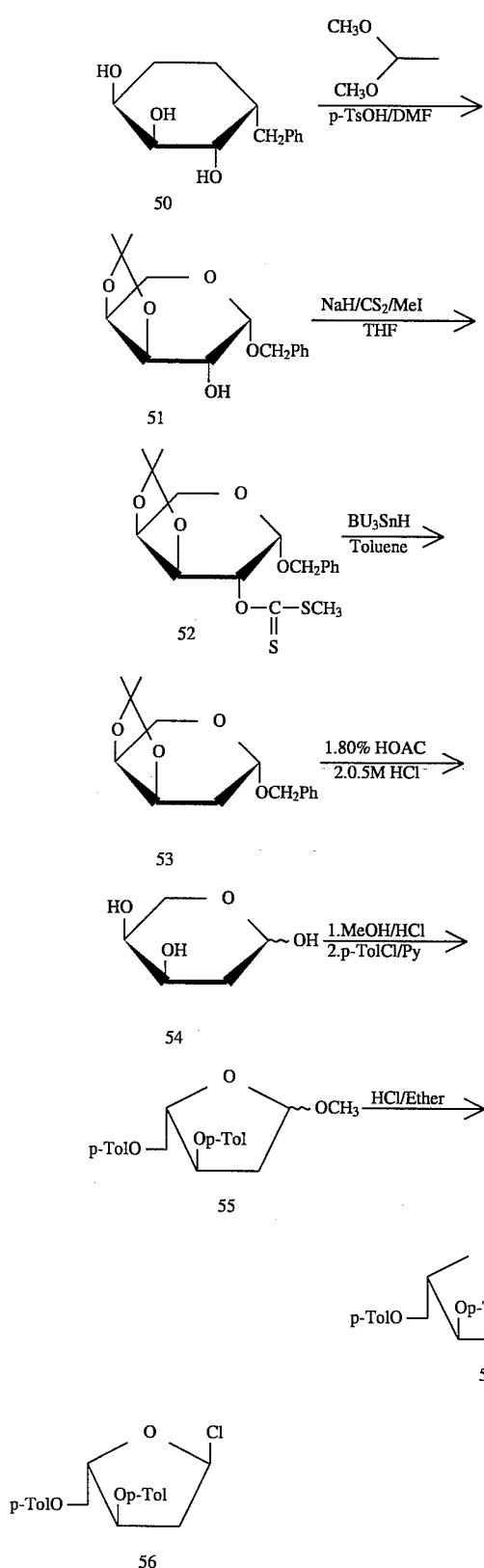

22
-continued
SCHEME VII

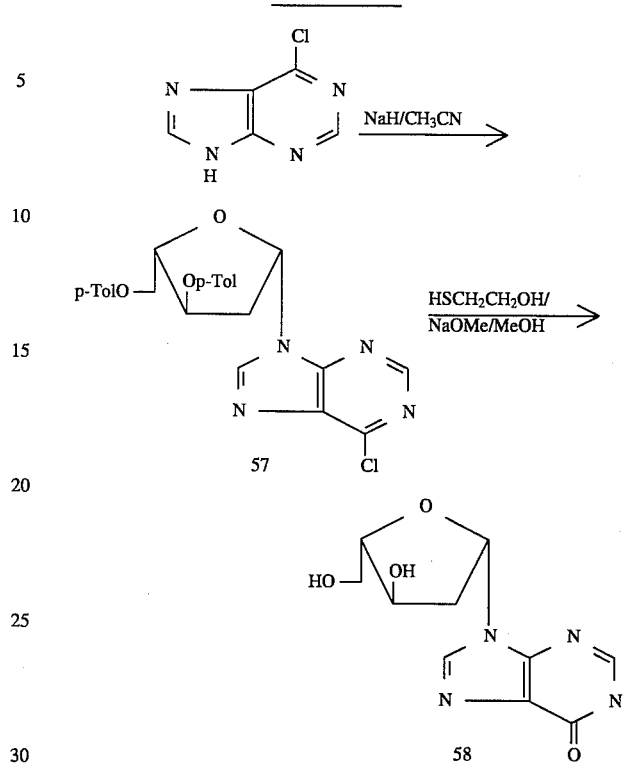

Other compounds within the scope of the invention can be made based on the teachings of the schematics provided herein, as well as the specific examples incorporated herein and in view with what is known to the skilled artisan.

In addition to the teachings provided herein, the skilled artisan will readily understand how to make compounds within the scope of the present invention by applying well known techniques such as those described in *Nucleic Acid Chemistry, Improved and New Synthetic Procedures, Methods and Techniques*, Edited by Leroy B. Townsend and R. Stuart Tipson, john Wiley & Sons, New York (1978); and *Chemistry of Nucleosides and Nucleotides*, Edited by Leroy B. Townsend, New York, Plenum Press (1988–1991). Suitable methods for making various substitutions on purine nucleosides are provided in WO90/08147. Suitable methods for making substitutions on pyrimidine nucleosides are provided in WO88/04662. The disclosure of both such applications being readily available to those skilled in the art and incorporated herein. Suitable methods for making substitutions within the sugar moiety of the presently claimed compounds are known to those skilled in the art and are described in various publications including: U.S. Pat. No. 4,880,782; WO88/00050; EP 199,451 A2; U.S. Pat. No. 3,817,982; Lange, P., et al, Progress in Antimicrobial and Anticancer Chemotherapy, *Proceedings of the 6th International Congress of Chemotherapy*, Univ. Park Press, England, 1970, Vol. p. 394–397; and Townsend, et al., supra, all of which are incorporated herein by reference.

This invention can be further understood by referring to the following Examples and Tables below:
Experimental

EXAMPLE 1

1-β-L-Ribofuranosyluracil

Step A

1-O-Acetyl-2,3,5-tri-O-benzoyl-β-L-ribose (2)

To a solution of L-ribose (5.0 g, 33.31 mmol) in MeOH (150 ml), concentrated $H_2SO_4$ (0.5 ml) was added and refluxed for 2 hours. After cooling the reaction mixture, pyridine (30 ml) was added and the solvents were evaporated. To the residue another 30 ml of pyridine was added and evaporated to dryness. The residue was dissolved in pyridine (50 ml) and $CH_2Cl_2$ (25 ml) then cooled to 0° C. and benzoyl chloride (19 ml, 166.55 mmol) was added dropwise and stirred at room temperature overnight. The solvents were evaporated and the residue dissolved in $CHCl_3$ and washed with $H_2O$ and $NaHCO_3$ and dried over anhydrous $Na_2SO_4$. After evaporating the $CHCl_3$, the residue was coevaporated with toluene to give a brown residue. The brown residue was dissolved in 30% HBr/OHAc (67 ml) and the solution was stirred at room temperature for 30 minutes, after which time glacial acetic acid (47 ml) was added and the mixture was cooled to 8° C. (internal temperature) in an ice-salt bath. Stirring and cooling were continued while $H_2O$ (34 ml) was added dropwise. The mixture was removed from the cooling bath and stirred another 30 minutes. Then the solvents were evaporated and the residue was dissolved in $CHCl_3$ and washed with $H_2O$ and $NaCHO_3$. The $CHCl_3$ was evaporated down to 50 ml, pyridine (50 ml) and acetic anhydride (9.5 ml) were added and stirred overnight at room temperature. Then the solvents were evaporated and the residue dissolved in $CHCl_3$, washed with $H_2O$ and $NaHCO_3$. After evaporation of the solvent a brown residue was obtained and it was coevaporated with toluene. The brown residue was triturated with EtOH to give light brown crystals. This was recrystallized from EtOH/EtOAc (5:2) to give 2 (8.15 g, 48.5%) as white crystals: m.p. 126°–127° C.

Step B 1-(2,3,5-Tri-O-benzoyl-β-L-ribofuranosyl)uracil (3)

A mixture of uracil (0.44 g, 3.96 mmol) and $(NH_4)_2SO_4$ (catalytic amount) in HMDS (25 ml) was refluxed for five hours. The resulting solution was concentrated under anhydrous conditions to yield silylated uracil. To a cooled (0° C.) and stirred solution of silylated uracil and 2 (1.0 g, 1.98 mmol) in dry dichloroethane (50 ml), TMSOTf (0.77 ml, 3.96 mmol) was added. The reaction mixture was warmed to room temperature and stirred for 16 hours. The reaction was quenched with saturated $NaCHO_3$ solution (5 ml) and evaporated to dryness. The residue was dissolved in EtOAc (100 ml), washed with water, brine, dried, filtered and evaporated to give a solid residue and it was purified on a silica gel column using EtOAc/$CHCl_3$ (30–40%) to give a white solid which was crystallized from EtOH/petroleum ether to give pure 3 (0.914 g, 82.7%) as white crystals: m.p. 143°–144° C.

Step C

1-β-L-Ribofuranosyluracil (4)

Compound 3 (0.87 g, 1.56 mmol) in $NH_3$/MeOH (100 ml) was stirred at room temperature overnight. The solvent was evaporated and the residue was dissolved in $H_2O$ (50 ml), washed with ether (3×25 ml). and evaporated to give a white solid and it was crystallized from 95% EtOH to give pure compound 4 (0.335 g, 87.2%) as white crystal: m.p. 165°–166° C.

EXAMPLE 2

1-β-L-Ribofuranosyl-5-fluorouracil

Step A 1-(2,3,5-Tri-O-benzoyl-β-L-ribofuranosyl)-5-fluorouracil (5)

To a mixture of 5-fluorouracil (0.85 g, 6.54 mmol) and compound 2 (3.0 g, 5.94 mmol) in anhydrous MeCN (100 ml) were successively added HMDS (1.25 ml, 5.95 mmol), $ClSiMe_3$ (0.6 ml, 4.76 mmol) and $SnCl_4$ (0.83 ml, 7.13 mmol). The resulting clear solution was refluxed for 1 hour when TLC indicated completion of the reaction. The solvent was evaporated and the residue dissolved in EtOAc (250 ml), washed with $NaHCO_3$ and $H_2O$. The EtOAc layer was dried, filtered and evaporated to give a white solid and it was crystallized from $CHCl_3$/MeOH (1–2%) to give compound 5 (2.11 g, 61.9%) as white crystals: m.p. 208°–209° C.

Step B

1-β-L-Ribofuranosyl-5-fluorouracil (6)

Compound 5 (0.75 g, 1.30 mmol) in $NH_3$/MeOH (100 ml) was stirred at room temperature overnight and worked up as in Example 1, Step C to give pure 6 (0.33 g, 96%) as white crystals: m.p. 147°–148° C.

EXAMPLE 3

1-β-L-Ribofuranosylcytosine

Step A 1-(2,3,5-Tri-O-benzoyl-β-L-ribofuranosyl)-$N^4$-acetylcytosine (7)

To a mixture of $N^4$-acetylcytosine (0.18 g, 1.19 mmol) and compound 2 (0.50 g, 0.99 mmol) in anhydrous MeCN (30 ml) were successively added HMDS (0.17 ml, 0.79 mmol), $ClSiMe_3$ (0.10 ml, 0.79 mmol) and $SnCl_4$ (0.14 ml, 1.19 mmol). The resulting clear solution was refluxed for one hour. Then the solvent was evaporated and the residue dissolved in EtOAc (100 ml), washed with $NaHCO_3$ and $H_2O$. After evaporation of the solvent the residue was purified on a silica gel column using EtOAc/petroleum ether (70%) to give pure 7 (0.41 g, 70%) as a white foam.

Step B

1-β-L-Ribofuranosylcytosine (8)

Compound 7 (0.85 g, 1.42 mmol) in $NH_3$/MeOH (100 ml) was stirred at room temperature overnight and worked up as in Example 1, Step C to give pure 8 (0.18 g, 52%) as white crystals: m.p. 210° C.

EXAMPLE 4

9-β-L-Ribofuranosyladenine

Step A 9-(2, 3, 5-Tri-O-benzoyl-β-L-ribofuranosyl)-6-chloropurine (9)

A mixture of 6-chloropurine (1.22 g, 7.93 mmol) and $(NH_4)_2SO_4$ (catalytic amount) in HMDS (25 ml ) was refluxed for eight hours. The resulting solution was concentrated under anhydrous conditions to yield silylated 6-chloropurine. To a cooled (0° C.) and stirred solution of silylated 6-chloropurine and 2 (2.0 g, 3.97 mmol) in dry dichloroethane (25 ml), TMSOTf (1.87 g, 1.6 ml, 7.93 mmol) was added. The reaction mixture was warmed to room temperature and stirred for 16 hours. The reaction was quenched with saturated $NaHCO_3$ solution (10 ml) and the solvent was evaporated. The residue was dissolved in EtOAc (150 ml), washed with water, brine, dried, filtered and evaporated to give a solid residue and it was purified on a silica gel column using CHCl$_3$:MeOH (5%) to give pure 9 (2.35 g, 99%) as foam.

Step B

9-β-L-Ribofuranosyladenine (10)

A solution of 9 (1.00 g) in DME/NH$_3$ (50 ml) was heated at 80° C. in a steel bomb for 24 hours. After cooling, the solvent was evaporated and the solid obtained was stirred in NH$_3$/MeOH (100 ml) overnight. After the evaporation of the solvent, the residue was dissolved in water (50 ml), washed with CHCl$_3$ (2×25 ml) and ether (2×25 ml). The water layer was evaporated and the residue crystallized from water to give pure 10 (0.30 g, 67%) as white crystals: m.p. 225° C. (dec).

EXAMPLE 5

9-β-L-Ribofuranosylhypoxanthine (11)

A mixture of 9 (1.05 g, 1.70 mmol), mercaptoethanol (0.48 ml, 6.9 mmol), and NaOMe in MeOH (100 ml) was refluxed for four hours. The reaction mixture was cooled, neutralized with glacial acetic acid and evaporated to dryness. The solid obtained was washed with CHCl$_3$ and the residue was crystallized from EtOH to give pure 11 (6.198 g, 47%) as white crystals: m.p. 212°–213° C. (dec).

EXAMPLE 6

9-β-L-Ribofuranosylguanine

Step A

9-(2,3,5-Tri-O-benzoyl-β-L-ribofuranosyl)-2-acetamido-6-chloropurine (12)

A mixture of 2-acetamido-6-chloropurine (1.68 g, 7.93 mmol) and (NH$_4$)$_2$SO$_4$ (catalytic amount) in HMDS (75 ml) was refluxed for 16 hours. The resulting clear solution Was concentrated under anhydrous conditions to yield silylated 2-acetamido-6-chloropurine. To a cooled (0° C.) and stirred solution of silylated 6-chloropurine and 2 (2.0 g, 3.96 mmol) in dry dichloroethane (100 ml), TMSOTf (1.6 ml, 7.93 mmol) was added. The reaction mixture was quenched with saturated NaHCO$_3$ solution (10 ml) and the solvent was evaporated. The residue was dissolved in EtOAc (150 ml), washed with water, brine, dried, filtered and evaporated to give a solid residue and it was purified on a silica gel column using EtOAc/petroleum ether (40–50%) to give pure 12 (1.38 g, 53%) as white foam.

Step B

9-β-L-Ribofuranosylguanine (13)

A mixture of 12 (0.58 g, 0.88 mmol), mercaptoethanol (0.25 ml, 3.53 mmol) and NaOMe (0.76 ml, 3.53 mmol, 35% weight solution in MeOH (10 ml)) was refluxed for six hours. The reaction mixture was cooled, neutralized with glacial acetic acid and evaporated to dryness. The solid obtained was washed with CHCl$_3$ and the residue was crystallized from water to yield pure 13 (0.215 g, 86%) as white crystal: m.p. 248° C. (dec).

EXAMPLE 7

9-β-L-Ribofuranosyl-6-thioguanine (14)

To a solution of 12 (0.68 g, 1.03 mmol) in anhydrous EtOH was added thiourea (0.15 g, 2.06 mmol). The reaction mixture was refluxed for an hour and then the solvent was evaporated. The residue was dissolved in EtOAc and washed with water and dried. After evaporation of the solvent the crude product was purified on a silica gel column (5% MeOH/CHCl$_3$) to yield benzoylated thioguanine. The product was debenzoylated by stirring with NH$_3$/MeOH (100 ml) at room temperature overnight. After evaporating the solvent the solid obtained was dissolved in water and washed with CHCl$_3$ (3×50 ml). Then the water was concentrated and crystallized from water to give pure 14 (0.15 g, 58%) as yellow crystals: m.p. 227° C. (dec).

EXAMPLE 8

2-Amino-α-L-ribofurano[1',2':4,5]oxazoline (15)

A mixture of L-ribose (7.0 g, 46.63 mmol), cyanamide (3.92 g, 93.27 mmol) and 1N NH$_4$OH (20 ml) was heated in a 30°–35° C. water bath until the solids were dissolved. The reaction mixture was kept at room temperature for 30 minutes and heated again at 60° C. for an hour, during which time a white solid started to precipitate. After adding MeOH (35 ml), this was kept in the refrigerator overnight, filtered and washed with MeOH and ether to give compound 15 (7.46 g, 92%) as white crystals: m.p. 195°–196° C. (dec).

EXAMPLE 9

O$^2$,O$^{2'}$-Anhydro-1-α-L-ribofuranosyluracil (16)

A mixture of compound 15 (7.86 g, 45.13 mmol) and methyl propiolate (14.04 ml, 157.95 mmol) in 50% EtOH (100 ml) was refluxed for six hours. After cooling, the solvent was evaporated to dryness and coevaporated twice with EtOH. Then the solid obtained was boiled in EtOH, cooled and filtered to give compound 16 (5.88 g, 57.6%) as white crystals: m.p. 215° C. (dec).

EXAMPLE 10

1-α-L-Ribofuranosyluracil (17)

A solution of compound 16 (4.50 g, 19.89 mmol) in 30 ml of 0.2N HCl was refluxed for two hours. After cooling, it was neutralized with Dowex (2×8–100) ion exchange resin. The resin was filtered and washed with water and the combined filtrates were evaporated and coevaporated with ethanol to give a hygroscopic foam, to which 1:1 mixture of acetone-ether (100 ml) was added and kept at room temperature for two days. This was filtered to yield compound 17 (4.80 g, 86.6%) as white solid: m.p. 137° C.

EXAMPLE 11

1-(2,3,5-Tri-O-benzoyl-α-L-ribofuranosyl)-4-thiouracil (19)

Step A

1-(2,3,5-Tri-O-Benzoyl-α-L-ribofuranosyl)uracil (18)

A solution of benzoyl cyanide (4.29 g, 32.76 mmol) in CH$_3$CN (25 ml) was added dropwise to a suspension of compound 17 (2.0 g, 8.19 mmol) in CH$_3$CN (50 ml) followed by Et$_3$N. The mixture was stirred at room temperature for three hours and the solvent was evaporated to dryness. The crude material obtained was purified on a silica column using 50% EtOAc/hexane as solvent to yield compound 18 (4.55 g, quantitative) as pale yellow foam.

Step B

1-(2,3,5-Tri-O-benzoyl-α-L-ribofuranosyl)-4-thiouracil (19)

Phosphorus pentasulfide (5.99 g, 26.95 mmol) was added to a solution of compound 18 (3.75 g, 6.73 mmol) in pyridine (70 ml) and was refluxed for four hours. After cooling, the solvent was evaporated and the residue dissolved in $CHCl_3$, washed with water and brine. After drying over anhydrous $Na_2SO4$, evaporation of the solvent gave the crude product which was purified on a silica gel column using 30% EtOAc/petroleum ether as solvent to give compound 19 (3.68 g, 95%) as golden yellow foam.

EXAMPLE 12

1-α-L-Ribofuranosylcytosine (20)

Compound 19 (3.68 g, 6.42 mmol) was treated with 200 ml of methanolic ammonia in a bomb at 100° C. for 18 hours. After cooling to room temperature, the solvent was evaporated to dryness and the residue dissolved in water (200 ml). The aqueous solution was extracted successively with $CHCl_3$ and $CCl_4$ (3×100 ml) to remove benzamide and methyl benzoate. The aqueous layer was treated with active charcoal, filtered through Celite®, evaporated to dryness and coevaporated with EtOH. The solid obtained was recrystallized from MeOH to give pure compound 20 (1.36 g, 81%) as white solid: m.p. 206°–207° C. (dec).

EXAMPLE 13

1-α-L-Ribofuranosyl-4-thiouracil (21)

Compound 19 (0.61 g, 1.06 mmol) in $NH_3$/MeOH (40 ml) was stirred at room temperature overnight. The solvent was evaporated and the residue was purified on preparative plates using MeOH/$CHCl_3$ (20%) to give pure compound 21 (0.185 g, 66.5%) as yellow foam.

EXAMPLE 14

1-α-L-ribofuranosyl-5-fluorouracil

Step A
1-Thio-2,3,5-tri-O-benzoyl-L-ribofuranoside (22)

To a solution of 2 (0.50 g, 0.99 mmol) in $CH_2Cl_2$ (50 ml), thiophenol (0.11 ml, 1.09 mmol) was added and stirred at room temperature for 15 minutes. Then the reaction mixture was cooled in an ice bath and $SnCl_4$ (0.07 ml, 0.59 mmol) was added dropwise and stirred at room temperature overnight. The reaction mixture was washed with 2N HCl (2×20 ml), water (25 ml), $NaHCO_3$ solution (25 ml) and then with brine. After drying over $Na_2SO_4$, the solvent was evaporated and the residue was purified on a silica gel column using 15–20% EtOAc/petroleum ether as solvent to give pure compound 22 (0.45 g, 82%) as an oil.

Step B
1-Thio-2,3,5-tri-O-benzyl-L-ribofuranoside (23)

To a solution of 22 (0.45 g, 0.81 mmol) in MeOH (20 ml), NaOMe (0.03 ml, 0.16 mmol) was added and stirred for 18 hours. The reaction mixture was neutralized by Dowex 50 ion exchange resin, filtered and evaporated. To this residue, DMF (20 ml) was added and cooled in an ice bath. To this cooled solution NaH (0.32 g, 8.11 mmol) was added in portion and stirred for 15 minutes. Benzyl bromide (0.96 ml, 8.11 mmol) was added dropwise and stirred at 0° C. for 2–3 hours. The reaction was quenched with water after diluting with EtOAc. The EtOAc layer was washed with water (2×25 ml) and brine. After drying and evaporation of the solvent, the crude product obtained was purified on a silica gel column using 5–10% EtOAc/petroleum ether as solvent to yield pure 23 (0.30 g, 73.5%) as an oil.

Step C
1-(2,3,5-Tri-O-benzyl-α-L-ribofuranosyl)-5-fluorouracil (24)

A mixture of 5-fluorouracil (0.15 g, 1.17 mmol) in hexamethyldisilazane (30 ml) and ammonium sulfate (catalytic amount) was refluxed for four hours. The resulting clear solution was concentrated in vacuo to yield silylated 5-fluorouracil as colorless oil. To a solution of silylated 5-fluorouracil in $CH_2Cl_2$ (20 ml) under nitrogen atmosphere were added NBS (0.11 g, 0.64 mmol), 4 Å molecular sieves (0.21 g) and compound 23 (0.30 g, 0.58 mmol) in $CH_2Cl_2$ (20 ml). The reaction mixture was stirred at room temperature overnight and quenched with the addition of $Na_2S_2O_3$ solution. The organic layer was washed with water, brine and dried over $Na_2SO_4$. Evaporation of the solvent gave the crude product and it was purified on a silica gel column using 5% MeOH/$CH_2Cl_2$ as solvent to give the pure α isomer 24 (0.23 g, 74.5%) as yellow oil.

Step D
1-α-L-ribofuranosyl-5-fluorouracil (25)

To a solution of 24 (1.0 g, 1.87 mmol) in $CH_2Cl_2$ (50 ml), at –78° C. under nitrogen atmosphere, 1M solution of $BCl_3$ (20 ml, 20.57 mmol) was added dropwise. The reaction mixture was stirred at –78° C. for four hours, a 1:1 mixture of $CH_2Cl_2$/MeOH (50 ml) was added and the reaction mixture was brought to room temperature and the solvents were evaporated to dryness. The residue was coevaporated with MeOH (25 ml) 5 times. The residue obtained was dissolved in water and washed with $CHCl_3$ (2×50 ml). The water layer was evaporated to give a white solid which was crystallized from EtOH/ether to give the pure 25 (0.41 g, 83%) as white crystals: m.p. 150° C.

EXAMPLE 15

2-Amino-β-L-arabinofurano[1',2':4,5]oxazoline (26)

A mixture of L-arabinose (10.0 g, 66.60 mmol), cyanamide (5.60 g, 133.20 mmol), methanol (30 ml) and $NH_4OH$ (3.3 ml) was stirred at room temperature for three days and then kept at –10° C. overnight. The product was collected with suction, washed with methanol and ether to give compound 26 (9.60 g, 82.7%) as white crystals: m.p. 175° C.

EXAMPLE 16

$O^2$, $O^{2'}$-Anhydro-β-L-arabinofuranosyluracil (27)

A solution of compound 26 (15.0 g, 85.15 mmol) and methyl propiolate (23.0 ml, 261.75 mmol), in 50% aqueous ethanol (250 ml) was refluxed for five hours. After cooling, the solvent was evaporated to dryness and the solid obtained was coevaporated with EtOH twice. Then the residue was dissolved in hot EtOH, cooled and filtered to give 27 (12.52 g, 65%) as white solid: m.p. 236° C.

EXAMPLE 17

2'-Deoxy-β-L-uridine (31)

Step A
3', 5'-Di-O-benzoyl-$O^2$, $O^{2'}$-anhydro-β-L-uridine (28)

A suspension of compound 27 (12.52 g, 55.31 mmol) and benzyl cyanide (15.96 g, 121.77 mmol), in DMF (100 ml) was treated dropwise with triethylamine (1.9 ml). The mixture dissolved rapidly and spontaneously deposited the product. The mixture was diluted with DMF (50 ml), stirred for three hours and finally diluted with ethanol (15 ml). This was poured into ether (250 ml), the precipitate collected with suction, washed with ether and dried to give 28 (21.92 g, 88%) as white solid: m.p. 260° C.

Step B

3',5',-Di-O-benzoyl-2'-chloro-2'-deoxy-β-L-uridine (29)

A mixture of compound 28 (21.72 g, 50.46 mmol), DMF (200 ml) and 6M HCl in DMF (40.5 ml) was stirred at 100° C. for 90 minutes under exclusion of atmospheric moisture, cooled down and poured under stirring into 1.5 L of water. The precipitate was collected with suction, washed with 1 L of water and recrystallized from ethanol (600 ml) to give pure 29 (19.9 g, 83.7%) as white crystals: m.p. 166°–167° C.

Step C

3',5',-Di-O-benzoyl-2'-deoxy-β-L-uridine (30)

A mixture of compound 29 (18.89 g, 39.93 mmol), tri-n-butyltin hydride (44.3 ml. 159.7 mmol), benzene (400 ml), and azobisisobutyronitrile (0.160 g) was refluxed under stirring for one hour. After cooling, the solid was filtered and washed with benzene. This solid was portion-wise recrystallized from ethanol (3.2 L) to yield pure 30 (15.9 g, 91.3%) as white crystals: m.p. 223°–224° C.

Step D

2'-Deoxy-β-L-uridine (31)

To a solution of compound 30 (5.75 g, 13.17 mmol) in MeOH (75 ml) was added 4.62M NaOMe (3.17 ml) and the reaction mixture was stirred at room temperature overnight. Then the solvent was evaporated and the residue was dissolved in water (250 ml) and washed with ether (3×100 ml). The aqueous layer was neutralized with Dowex 50 (H+) ion exchange resin, filtered and evaporated. The crude product obtained was coevaporated with ethanol and crystallized from ethanol to give 31 (2.53 g, 84.3%) as white crystals: m.p. 162°–163° C.

EXAMPLE 18

3',5'-Di-O-benzoyl-2'deoxy-4-thio β-L-uridine (32)

The boiling solution of compound 31 (5.0 g, 11.45 mmol) in anhydrous dioxane was treated with phosphorus pentasulfide (2.58 g, 12.83 mmol) and the mixture refluxed under nitrogen atmosphere for 30 minutes. The mixture was then treated with additional phosphorus pentasulfide (2.85 g), refluxed for another 30 minutes, filtered while hot, and the solid washed with dioxane. The filtrate was evaporated to dryness and the crude product obtained was purified on a silica gel column using 20–30% EtOAc/petroleum ether as solvent to give an oil, which was coevaporated with ethanol and then crystallized from ethanol-petroleum ether to give pure 32 (2.62 g, 50.5%) as yellow crystals: m.p. 136°–137° C.

EXAMPLE 19

2'-Deoxy-β-L-cytidine (33)

Compound 32 (3.0 g, 6.63 mmol) was treated with 200 ml of methanolic ammonia in a bomb at 100° C. for 10 hours. After cooling to room temperature, the solvent was evaporated to dryness and the residue dissolved in water (200 ml). The aqueous layer was washed with ether (3×100 ml) and treated with active charcoal, filtered through Celite®, and evaporated to dryness and coevaporated with ethanol. The solid obtained was recrystallized from ethanolacetonitrile mixture (1:1.0) to give 33 (1.13 g, 75%) as white crystals: m.p. 210° C.

EXAMPLE 20

2'-Deoxy-β-L-4-thiouridine (34)

Compound 32 (0.25 g, 0.55 mmol) in $NH_3$/MeOH (30 ml) was stirred at room temperature overnight. The solvent was evaporated and the residue was purified on preparative plates using MeOH/$CHCl_3$ (20%) to give pure 34 (0.12 g, 88%) as yellow oil.

EXAMPLE 21

2'-Deoxy-β-L-thymidine (35)

Compound 31 (0.5 g, 2.19 mmol) was heated at 60°–70° C. for six days in a mixture of 1.2 ml 37% aqueous formaldehyde and 1.2 ml 1M KOH. Every 24 hours the reaction mixture was treated with an additional 0.55 ml of 1M KOH and 0.55 ml of aqueous formaldehyde. The solution was then diluted with water, adjusted to pH4 with Dowex 50($H^+$), filtered, the filtrate evaporated in vacuo and the residue coevaporated several times with ethanol. The final residue was dissolved in ethanol and made alkaline (pH10) by the addition of triethylamine, evaporated and coevaporated several times with toluene. The residue was dissolved in 22 ml ethanol and 50 μl concentrated hydrochloric acid was added. The solution was refluxed for five hours. Then the reaction mixture was made alkaline with triethylamine, evaporated and the residue was purified by flash-chromatography (20% methanol-chloroform). 240 mg pure product and 280 mg mixture (containing starting material) was obtained. The product was dissolved in 20 ml ethanol, acidified with 27 μl concentrated hydrochloric acid and hydrogenated over 55 mg of 10% palladium on charcoal catalyst overnight under atmospheric pressure. The mixture was filtered, the filtrate made alkaline with triethylamine and evaporated to dryness. Flash-chromatography of the residue (20% ethanol-chloroform) gave 35 (0.18 g, 34% overall yield) as a white powder.

EXAMPLE 22

2'-Deoxy-β-L-5-fluorouridine (39)

Step A

1-[3',5'-O-(1,1,3,3-Tetraisopropyldisiloxane-1,3-diyl)-β-L-ribofuranosyl]-5-fluorouracil (36)

To a stirred suspension of 6 (1.0 g, 3.90 mmol) in pyridine (40 ml) was added 1,3-dichloro-1,1,3,3-tetraisopropyldisiloxane (1.65 ml, 4.68 mmol). This was stirred at room temperature until the completion of the reaction (five hours), the solvent was evaporated and the residue was dissolved in EtOAc and washed with water, 5% HCl, water, saturated aqueous $NaHCO_3$ and brine. After drying over anhydrous $Na_2SO_4$ it was filtered and evaporated to give the crude product 36 and it was used in the next step without further purification.

Step B

1-[2'-O-Phenoxythiocarbonyl-3',5'-O-(1,1,3,3-tetraisopropyldisiloxane-1,3-diyl)-β-L-ribofuranolsyl]-5-fluorouracil (37)

To a solution of 36 (3.90 mmol) in anhydrous $CH_3CN$ (50 ml) was added 4-(dimethyl amino) pyridine (DMAP) (0.92 g, 7.56 mmol) and phenyl chlorothionoformate (0.6 ml, 4.29 mmol). The solution was stirred at room temperature for 24 hours. Then the solvent was evaporated and the residue was dissolved in EtOAc and washed with water, 5% HCl, water, saturated aqueous NaHCO₃ and brine. The EtOAc layer was dried (Na$_2$SO$_4$), filtered and evaporated. The resultant oil was purified on a silica gel column using MeOH/CHCl$_3$ (5%) to give pure 37 (0.47 g) as white foam.

Step C

3',5'-O-(1,1,3,3-Tetraisopropyldisiloxane-1,3-diyl) -β-L-5-fluorouridine (38)

To a mixture of 37 (0.46 g, 0.72 mmol), AIBN (0.02 g, 0.14 mmol) in dry toluene (30 ml) was added Bu$_3$SnH (2.0 ml, 5.05 mmol). The solution was deoxygenated with oxygen-free air and then heated at 75° C. for four hours. Then the solvent was evaporated and the residue was purified on a silica gel column using EtOAc/petroleum ether (30%) to yield pure 38 (0.34 g, 97%) as white foam.

Step D

2'-Deoxy-β-L-5-fluorouridine (39)

A mixture of 38 (0.32 g, 0.66 mmol) and TBAF (1.4 ml, 1M solution) in THF (15 ml) was stirred at room temperature. After completion of the reaction the solvent was evaporated and the residue was dissolved in water and washed with ether. The water was evaporated and the residue was purified on a silica gel column using MeOH/CHCl$_3$ (10%) to yield pure 30 (1.30 g, 80%) as an oil.

EXAMPLE 23

2'-Deoxy-β-L-5-fluorouridine (49)

Following the method of Example 22, this compound was made starting from 1-α-L-ribofuranosyl-5-fluorouracil (25): m.p. 150° C.

NMR: (DMSOd$_6$) δ 1.90 (m, 1H, H-2'a) 2.55 (m, 1H, H-2'b), 3.33 (m, 2H, H-5'), 4.19 (m, 2H, H-3'& 4'), 4.86 (br s, 1H, OH), 5.43 (br s, 1H, OH), 6.10 (dd, 1H, H-1'), 8.15 (d, 1H, H-6), 11.78 (br s, 1H, N-H).

EXAMPLE 24

2',3'-Dideoxy-β-L-uridine (43)

Step A

2'-Deoxy-5'-O-(4-monomethoxytrityl)-β-L-uridine (40)

To a solution of compound 31 (2.0 g, 9.16 mmol) in pyridine (100 ml), 4-monomethoxytrityl chloride (3.11 g, 10.08 mmol) was added and stirred at room temperature for 24 hours. Then the solvent was evaporated and the residue was dissolved in EtOAc, washed with water, NaHCO$_3$ and brine. After drying over anhydrous Na$_2$SO$_4$, the solvent was evaporated to give the crude product and it was purified on a silica gel column (5% MeOH/CHCl$_3$ )to yield 40 (4.13 g, 94%) as white foam.

Step B

2'-Deoxy-5'-O-(4-monomethoxytrityl)-3',O-phenoxythiocarbonyl-β-L-uridine (41)

To a solution of 40 (4.13 g, 8.25 mmol) in anhydrous CH$_3$CN (100 ml) was added DMAP (0.46 g, 3.76 mmol) and phenyl chlorothiono formate (1.26 ml, 9.07 mmol). The solution was stirred at room temperature for 24 hours. Then the solvent was evaporated and the residue was dissolved in EtOAc and washed with water, 5% HCl, water, saturated aqueous NaHCO$_3$ and brine. Evaporation of the EtOAc layer gave the crude product and it was purified on a silica gel column (3.5% MeOH/CHCl$_3$) to yield pure 41(3.95 g, 75%) as foam.

Step C

2',3'-Dideoxy-5'-O-(4-monomethoxytrityl)-β-L-uridine (42)

To a mixture of 41 (3.95 g, 6.20 mmol), AIBN (0.20 g, 1.24 mmol) in dry toluene (150 ml) was added Bu$_3$SnH (16.7 ml, 62.0 mmol). The solution was deoxygenated with oxygen-free air and then heated at 75° C. for five hours. The solvent was evaporated and the residue was chromatographed on a silica gel column (50–60% EtOAc/petroleum ether) to yield pure 42 (2.36 g, 78.8%) as white foam.

Step D

2',3'-Dideoxy-β-L-uridine (43)

Compound 42 (0.37 g, 0.76 mmol) in 80% acetic acid (5.0 ml) was stirred at room temperature for two hours, the solvent was evaporated and the residue was coevaporated with toluene. The residue was purified on a silica gel column (15% MeOH/CHCl$_3$) to give pure 43 and it was crystallized from MeOH/ether to give 43 (0.118 g, 73%) as white crystals: m.p. 122° C.

EXAMPLE 25

2'-Deoxy-β-L-inosine (58)

Step A 9-(2-Deoxy-3,5-di-O-p-toluoyl-β-L-ribofuranosyl)-6-chloropurine (57)

A mixture of 6-chloropurine (0.40 g, 2.62 mmol) and sodium hydride (60% in oil, 0.11 g, 2.88 mmol) in anhydrous CH$_3$CN (50 ml) was stirred under a nitrogen atmosphere for 30 minutes at room temperature. Crystalline compound 56, made according to the procedure described in *Tetrahedron* 43, 2355–2368, 1987, for the D-isomer (0.85 g, 2.18 mmol), was added and stirring was continued for 2 hours. After addition of CHCl$_3$ (50 ml), the mixture was filtered through Celite®. The filtrate was evaporated and the crude was purified on a silica gel column using 50% EtOAc/petroleum ether to give pure compound 57 (0.55 g, 50%) as white solid.

Step B

2'-Deoxy-β-L-inosine (45)

A mixture of 57 (0.20 g, 0.39 mmol), mercaptoethanol (0.11 ml, 1.55 mmol), and NaOMe (0.34 ml, 1.55 mmol) in MeOH was refluxed for four hours. The reaction mixture was cooled, neutralized with glacial acetic acid and evaporated to dryness. The solid obtained was washed with CHCl$_3$ and the residue was crystallized from H$_2$O/MeOH to give pure 58 (0.070 g, 71%) as white crystals: m.p. 219°–220° C.

Utility

In vitro activity against certain human tumor cell lines.

CELL LINES: Eight different established human cell lines CALU (lung), COLO320 (colon), H578St (breast), HT-29 (colon), MCF-7 (breast), OM-1 (colon), SKLU (lung) and SKMES(lung), and two control cell lines (bone marrow and/or fibroblast cells) were utilized. All cell lines were obtained from the Tumor Cloning Laboratory, Institute for Drug Development, Cancer Therapy and Research Center, San Antonio, Tex. All cell lines grew as monolayers in the appropriate culture medium supplemented with heat-inactivated calf serum. All reagents were obtained from Grand Island Biological Co., Grand Island, N.Y.

IN VITRO EXPOSURE OF TUMOR CELLS TO COMPOUNDS: Stock solutions of intravenous (iv) formulations of certain of the compounds of the present invention (as shown in Table I below), as well as intravenous formulations of 5-FU (control) were used. The iv formulations of the compounds of the present invention were prepared with sterile buffered saline and stored at −70° C. until required for testing. The 5-FU control formulation was prepared as suggested in the product literature.

Following trypsinization, tumor cells were suspended in tissue culture medium and exposed to the antitumor agents continuously at three different concentrations: 10, 1 and 0.1 μg/ml.

RADIOMETRIC MEASUREMENT OF GROWTH INHIBITION: Growth inhibition was assessed with the BACTEC System 460 (Johnston Laboratories, Towson, Md.) after addition of the antitumor agent to the cell in the respective growth medium containing $^{14}$C-glucose at a final concentration of 2 μCi/ml. (See generally, C. Arteaga, et al., *A Radiometric Method for Evaluation of Chemotherapy Sensitivity: Results of Screening a Panel of Human Breast Cancer Cell Lines*, Cancer Research, 47, 6248–6253 (1987).

Two mls of the tumor cell suspension containing radioactive glucose were seeded into sterile, disposable 15 ml vials by injection through self-sealing rubber-aluminum caps. For each cell line, the optimal number of tumor cells needed per vial in order to show significantly measurable growth in this radiometric system varied. The seeded vials were then incubated at 37° C. Measurement of the release of $^{14}CO_2$ resulting from the metabolism of $^{14}$C-glucose were performed on days 6, 9, 12 and 15 in the BACTEC instrument. This instrument flushes the $^{14}CO_2$ containing air out of the vials into an ionization chamber that converts dpm to growth index values. Chemotherapy sensitivity was calculated by comparing the growth index values of drug-treated vials to that observed in control vials. Each data point represents triplicate values.

Results are shown in Table I below.

TABLE I

| COMPOUND | % SURVIVAL BONE MARROW | % SURVIVAL TUMOR | | IC 50 |
|---|---|---|---|---|
| 5-FU |  | CALU | 2.2 | <0.6 |
|  | 1.9 | COLO320 | 1.0 | <0.6 |
|  |  | HS578T | 43.5 | <0.6 |
|  |  | HT29 | 1.2 | 0.613 |
|  |  | MCF-7 | 0.8 | <0.6 |
|  |  | OM-1 | 1.7 | 1.47 |
|  |  | SKLU | 5.0 | 1.05 |
|  |  | SKMES | 11.2 | <0.6 |
| α-L-ribofuranosyl-uracil | 96.6 | CALU | 89.1 | >10 |
| 2-amino-α-L-ribofurano[1',2':4,5]oxazoline | 114.6 | OM-1 | 2.6 | 0.026 |
| 2-amino-α-L-arabinofurano[1',2':4,5]oxazoline | 109.5 | CALU | 89 | 44.6 |
|  |  | MCF-7 | 88.8 | 187 |
|  |  | OM-1 | 41.3 | 5 |
| $O^2,O^{2'-\text{anhydro}}$-1-α-L-ribofuranylosyl uracil | 70.9 | OM-1 | 46.4 | 2.97 |
| α-L-ribofuranosyl cytosine | 120.1 | COLO320 | 82.3 | 34.9 |
|  |  | SKLU | 88.8 | 240 |
| 1-(2,3,5-tri-O-benzoyl-α-L-ribofuranosyl)-4 thiouracil | 85.9 | HT29 | 75 | >10 |
| 1-(3,5-di-O-benzoyl-2-deoxy-β-L-ribofuranosyl)-4-thiouracil | 102.1 | MCF-7 | 84.5 | >10 |
|  |  | OM-1 | 35.7 | 0.98 |
|  |  | SKLU | 77.7 | 88.7 |
| 2'-β-L-deoxy ribofuranosyl-4-thiouracil | 98.2 | OM-1 | 82.3 | 34.3 |
|  |  | SKLU | 79.4 | >10 |
| α-L-ribofuranosyl-5-fluorouracil | 94.6 | OM-1 | 0.4 | 0.87 |
|  |  | SKLU | 71 | 43.4 |
| β-L-ribofuranosyl-5-fluorouracil | 129.9 | COLO320 | 81.9 | 188 |
|  |  | HT29 | 64.7 | 51 |
|  |  | OM-1 | 71.9 | 37.8 |
|  |  | SKLU | 69.7 | 32.2 |
| β-L-ribofuranosyl cytosine | 72.6 | OM-1 | 39.2 | 5.9 |
| β-L-ribofuranosyl guanine | 169.8 | HT29 | 80.9 | >10 |
|  |  | OM-1 | 44.7 | 0.097 |
| 2'-α-L-deoxy ribofuranosyl-5-fluorouracil | 104 | HT29 | 81.7 | 85.2 |
|  |  | MCF-7 | 66.9 | 16.6 |
|  |  | OM-1 | 66.7 | 62.9 |
|  |  | SKLU | 83.9 | 32.5 |
| 2'-β-L-deoxy ribofuranosyl thymine | 158.9 | COLO320 | 67.0 | 57.4 |
|  |  | HT29 | 72.2 | 30.4 |
|  |  | OM-1 | 37.6 | 6.5 |
|  |  | SKLU | 72.4 | 38.2 |
| β-L-ribofuranosyl uracil | 112.5 | HT29 | 78.7 | >10 |
|  |  | OM-1 | 30.8 | 0.094 |
| 2',3'-β-L-dideoxy ribofuranosyl uracil | 79.8 | CALU | 0.4 | 0.623 |
| β-L-ribofuranosyl adenine | 91.2 | OM-1 | 50.9 | 4.23 |
| β-:-ribofuranosyl hypoxanthine | 118.4 | COLO320 | 68.2 | 17.9 |
|  |  | HS578T | 93.4 | >10 |
|  |  | MCF-7 | 96.8 | 38.1 |
|  |  | OM-1 | 87.3 | 82.7 |
|  |  | SKLU | 82.5 | 48.1 |
| β-L-ribofuranosyl-6-thioguanine | 97.4 | HS578T | 66.6 | 17.1 |
|  |  | OM-1 | 83.1 | 42.7 |
|  |  | SKLU | 45.1 | 8.7 |
| 2'-β-L-deoxy ribofuranosyl 5-fluorouracil | 108.8 | COLO320 | 19.6 | 6.56 |
|  |  | HT29 | 42.5 | 8.46 |
|  |  | MCF-7 | 86.9 | 60.7 |
|  |  | OM-1 | 85.2 | 56.1 |
|  |  | SKLU | 86.2 | 59.9 |
| 2'-β-L-deoxy ribofuranosyl adenine | 64.9 | CALU | 28.9 | 0.696 |
| 2'-β-L-deoxy ribofuranosyl hypoxanthine | 109.6 | OM-1 | 83.1 | >10 |

The data presented in Table I are compared to results achieved with 5-FU as the control. All compounds were dosed on an equimilimolar basis. Inhibitory concentration (IC 50) is defined as the concentration required to kill 50% of the untreated cancer cells.

Although the IC 50 of certain of the compounds listed in Table I may be higher than that for 5-FU (the control), the compounds of the present invention are generally less toxic to normal cells such as bone marrow or fibroblasts. This implies that the compounds of the present invention may have advantages over known cancer therapies as the claimed compounds may be less toxic and/or more selective for the tumor cells, thereby causing less serious side effects. Additionally, because of their lower toxicity to normal cells, it is anticipated that the present compounds may be dosed at a higher rate to selectively increase toxicity to the cancer cells. In this regard, a therapeutic ratio for a given compound is typically determined by the following calculation.

$$\frac{\% \text{ survival bone marrow}}{\% \text{ survival tumor}}$$

A therapeutic ratio of <80% is considered active.

In Vivo Evaluation

Representative compounds of the present invention are being tested in a variety of preclinical tests of anti-cancer activity which are indicative of clinical utility. For example, certain compounds will be tested in vivo against human tumors xenografted into nude mice, specifically B16, MX-1 and P388 Leukemia tumor lines were used.

B16 Melanoma

B6D2F1 mice receive i.p. inocula of B16 murine melanoma brei prepared from B16 tumors growing s.c. in mice (day 0). On day 1, tumored mice are treated with drugs or vehicle control; the drugs, route of drug administration and schedule are selected as appropriate for the study in question. If dosing information for agents is not available, the maximum tolerated dose (MTD) is determined in initial dose-finding experiments in non-tumored mice. In a typical experiment, drugs are given at their MTD and ½ MTD doses i.p. on a daily×5 schedule.

The mean survival times of all groups are calculated and results are expressed as mean survival of treated mice/mean survival of control mice (T/C)×100. A T/C value of 150 means that the treated group lived 50% longer than the control group; this is sometimes referred to as the increase in life span, or ILS value.

Mice that survive for 60 days are considered long term survivors, or cures, in the B16 model. The universally accepted cut-off for activity in this model, which has been used for years by the NCI, is T/C=125. Conventional use of B16 over the years has set the following levels of activity: T/C<125, no activity; T/C=125–150, weak activity; T/C=150–200, modest activity; T/C=200–300, high activity; T/C>300, with long term survivors' excellent, curative activity.

Statistics are performed on the data using primarily the log rank p-value test.

P388 Leukemia

This test is conducted in exactly the same way as the B16 test. The tumor inoculum is prepared by removing ascites fluid containing P388 cells from tumored DBA/2 mice, centrifuging the cells, and then resuspending the leukemia cells in saline. Mice receive 1×10$^5$ P388 cells i.p. on day 0.

MX-1 Human Breast Tumor Xenograft

Nude mice are implanted s.c. by trocar with fragments of MX-1 mammary carcinomas harvested from s.c. growing MX-1 tumors in nude mice hosts. When tumors are approximately 5 mm×5 mm in size (usually about ten days after inoculation), the animals are pair-matched into treatment and control groups. Each group contains 10 tumored mice, each of which is ear-tagged and followed individually throughout the experiment. The administration of drugs or vehicle begins the day the animals are pair-matched (day 1). The doses, route of drug administration and schedule are selected as appropriate for the study in question. If the MTD dose of an agent is not known, it is determined in an initial dosing experiment in non-tumored mice. In a typical experiment, drugs are given at their MTD and ½ MTD doses i.p. on a daily×5 schedule.

The experiment is usually terminated when control tumors reach a size of 2–3 g. Mice are weighed twice weekly, and tumor measurements are taken by calipers twice weekly, starting on day 1. These tumor measurements are converted to mg tumor weight by a well-known formula, and from these calculated tumor weights the termination date can be determined. Upon termination, all mice are weighed, sacrificed, and their tumors excised. Tumors are weighed and the mean tumor weight per group is calculated. In this model, the mean control tumor weight/mean treated tumor weight×100% (C/T) is subtracted from 100% to give the tumor growth inhibition (TGI) for each group.

Some drugs cause tumor shrinkage in the MX-1 model. With these agents, the final weight of a given tumor is subtracted from its own weight at the start of treatment on day 1. This difference divided by the initial tumor weight is the % shrinkage. A mean % tumor shrinkage can be calculated from data from the mice in a group that experienced MX-1 regressions. If the tumor completely disappears in a mouse, this is considered a complete regression or complete tumor shrinkage. If desired, mice with partial or total tumor regressions can be kept alive past the termination date to see whether they live to become long term, tumor-free survivors.

Statistics are performed on the data using primarily the log rank p-value test.

Protocols for HIV-1 Inactivation Studies

General protocols for the testing of compounds in in vitro antiviral screens are disclosed in the following references:

1) Perez, V. L., Rowe, T., Justement, J. S., Butera, S. T., June, C. H. and Folks, T. M., An HIV-1-infected T cell clone defective in IL-2 production and Ca$^{++}$ mobilization after CD3 stimulation, *J. Immunol.* 147:3145–3148, 1991.

2) Folks, T. M., Justement, J., Kinter, A., Dinarello, C. and Fauci, A. S., Cytokine-induced expression of HIV-1 in a chronically infected promonocyte cell line, Science 238:800–802, 1987.

3) Folks, T. M., Clouse, K. A., Justement, J., Rabson, A., Dub, E., Kehrl, J. H. and Fauci, A. S., Tumor necrosis factor α induces expression of human immunodeficiency virus in a chronically infected T-cell clone, *Proc. Natl. Acad. Sci. USA* 86:2365–2368, 1989.

4) Clouse, K. A., Powell, D., Washington, I., Poli, G., Strebel, K., Farrar, W., Barstad, P., Kovacs, J., Fauci, A. S. and Folks, T. M., Monokine regulation of human immunodeficiency virus-1 expression in a chronically infected human T cell clone, *J. Immunol.* 142:431–438, 1989.

1. Inactivation of cell-free HIV-1.

Cell-free HIV-1 stocks are derived from culture supernatants of H-9 human T cells chronically infected with the HTLV-IIIB strain of HIV-1. Other HIV-1 strains including the MN and some African strains may be used later for confirmatory purposes.

a) Cell-free HTLV-IIIB:

Cell-free HIV-1 (5×10$^5$ to 1×10$^6$ TCID$_{50}$/ml, or median tissue culture infectious dose) is either left untreated, or treated with RPMI 1640 culture medium, or with different concentrations of antivirals for various time intervals at 37° C., or at a temperature to be determined. After incubation, the treated and untreated stocks are added to 5×10$^5$ washed and pelleted target MT-4 cells. After 1 h incubation at 37° C., the MT-4 cells are washed three times with RPMI 1604, resuspended in RPMI 1640 supplemented with 15% fetal bovine serum (FBS), and cultured in a 5% CO$_2$ humidified incubator at 37° C. Cell viability is determined on day 7 of culture by the addition of the 3-(4,5-dimethyl-thiazol-2-yl)-2, 5-diphenyitetrazolium bromide (MTT) dye, which changes in color in the presence of live mitochondria. All determinations are done in triplicates.

b) Cell-free JR-CSF:

In addition to assessing the effects of antivirals on a lab strain of HIV-1 (HTLV-IIIB), it is also important to determine antiviral effects on a primary isolate of HIV-1 (JR-CSF), which only infects primary human peripheral mononuclear cells (PBMCs). Human PBMCs activated with phytohemagglutinin A (PHA, Sigma Chemical Co.) are prepared by culturing PBMCs in RPMI 1640 culture medium supplemented with 10% FBS (complete medium) and 2.0 µg of PHA/ml for 1 day before used in infectivity studies. HIV-1 (JR-CSF) untreated or treated as above are added to PHA-activated human PBMCs and incubated for 1 h at 37° C. After incubation, 1.0 ml of complete RPMI 1640 culture medium is added to the cells. Culture supernatants are collected on days 3, 6 and 9 of culture, and the amounts of HIV-1 p24 core protein are determined in triplicate by the HIV-1 p24 antigen capture assay (Coulter Immunology, Fla., or NEN-DuPont, Wilmington, Del.).

2. Inactivation of cell-associated HIV-1.

HIV-1-infected human cells to be used include the chronically infected H-9 cells (HTLV-IIIB or FIN strains), and human PBMCs infected with HTLV-IIIB or with JR-CSF. HTLV-IIIB and MN infected H-9 cell lines are available from various laboratories including those listed in the references cited above. For infected human PBMos, fresh human PBMCs are obtained from normal volunteers and stimulated with PHA, then infected with HTLV-IIIB or JR-CSF, as described above. On day 7 after in vitro infection, infectivity is checked by testing for the presence of HIV-1 p24 in the culture supernatants. Infected cultures are divided in equal aliquots. One set is then treated with antivirals at different concentrations for various time intervals, whereas one set is left untreated. Culture supernatants collected on days 3, 6 and 9 of culture will be assessed for HIV-1 p24 levels by the p24 antigen capture assay kit. Cells from these cultures can also be used in immunofluorescence (IF) studies to determine the percentage of cells expressing HIV-1 antigen(s).

3. Inactivation of HIV-1 latently infected cells.

These assays are designed to study the effects of antivirals on HIV-1 latently infected cells. One or more of the following HIV-1 latently infected human cell lines can be used (J1-1, U1/HIV and ACH-2 obtained from the NIH AIDS Research and Reagent Reference Program, Rockville, Md.). These cells are characterized by HIV-1 infection without significant HIV-1 viral replication unless they are stimulated with different cytokines which results in a 10–100 fold increase in HIV-1 replication. J1-1, or U1/HIV, or ACH-2 cells are seeded in 96-well round-bottom tissue culture plates to give $5\times10^5$/well in RPMI 1640 supplemented with 15% fetal bovine serum (FBS). The cells are either left untreated or treated with different concentrations of antivirals for various time intervals. Subsequent to treatment, treated and untreated cells are washed three times in RPMI 1640 and are stimulated as follows.

The J1-1 cells are stimulated with 1000 U of α tumor necrosis factor (α-TNF, Genzyme) for 48 h at 37° C. as previously described (Reference 1).

The U1/HIV-1 cells are stimulated with 20%–40% PHA-culture supernatant (Electronucleonics) for 48h at 37° C. (Reference 2). The PHA-supernatant will either be purchased from Electronucleonics or will be prepared in our laboratory. To prepare PHA-supernatant, normal human PBMC will be cultured at a cell density of $10^6$ cells/ml in RPMI 1640 supplemented with 15% FBS and 10 µg/ml of phytohemagglutinin A (PHA, Sigma Chemical Co.). The culture supernatant will be harvested, filtered through a 2 µm filter and used to stimulate the U1/HIV cells as described above.

The ACH-2 cells will be stimulated by addition of 1.0 µM of phorbal 12-myristate 13 acetate (PMA, Sigma Chemical Co.) for 48 h at 37° C. as described (References 3 and 4 above). At the end of the stimulation period, culture supernatants are collected and HIV-1 expression is assessed by the HIV-1 p24 antigen capture ELISA (DuPont) and by the reverse transcriptase (RT).

In inactivation of cell-associated HIV-1 experiments, the treated and untreated cells could also be submitted to PCR analysis.

4. Inhibition of HIV-1-induced syncytium formation.

HIV-1-infected H-9 cells are left untreated or treated with antiviral as described above. Treated and untreated cells ($5\times10^4$ cells/well) are added to 96-well flat-bottom microtiter tissue culture plates containing $1\times10^5$ indicator SupT1 human T cells/well in complete RPMI 1640 culture medium. Following overnight incubation at 37° C., syncytium formation is scored by two independent people using an inverted microscope scope.

5. Cytotoxicity Studies.

The cytotoxicity of the antivirals can be tested on a variety of cell types. All of the cell lines used above and normal human PBMCs are incubated with different antiviral concentrations for various time intervals as described above. Cytotoxicity is determined by the MTT dye method (see above) and by [$^3$H] thymidine uptake and scintillation counting.

Dosage and Formulation

The antitumor compounds (active ingredients) of this invention can be administered to inhibit tumors by any means that produces contact of the active ingredient with the agent's site of action in the body of a mammal. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

The dosage administered will be a tumor-inhibiting amount of active ingredient and will, of course, vary depending upon known factors, such as the pharmacodymanic characteristics of the particular active ingredient and its mode and route of administration; age, health and weight of the recipient; nature and extent of symptoms; kind of concurrent treatment, frequency of treatment and the effect desired. Usually a daily dosage (therapeutic effective amount or cancer-inhibiting amount) of active ingredient can be about 5 to 400 milligrams per kilogram of body weight. Ordinarily, 10 to 200, and preferably 10 to 50, milligrams per kilogram per day given in divided doses 2 to 4 times a day or in sustained release form is effective to obtain desired results.

Dosage forms (compositions) suitable for internal administration contain from about 1 milligram to about 500 milligrams of active ingredient per unit. In these pharmaceutical compositions the active ingredient will ordinarily be present in an amount of about 0.05–95% by weight, based on the total weight of the composition.

The active ingredient can be administered orally in solid dosage forms such as capsules, tablets and powders, or in liquid dosage forms such as elixirs, syrups and suspensions. It can also be administered parenterally, in sterile liquid dosage forms.

Gelatin capsules contain the active ingredient and powdered carriers such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain, preferably, a water soluble salt of the active ingredient, suitable stabilizing agents and, if necessary, buffer substances. Antioxidizing agents such as sodium bisulfate, sodium sulfite or ascorbic acid, either alone or combined are suitable stabilizing agents. Also used are citric acid and its salts, and sodium EDTA. In addition, parenteral solutions can contain preservatives such as benzalkonium chloride, methyl- or propyl-paraben and chlorobutanol, Suitable pharmaceutical carriers are described in *Remington's Pharmaceutical Sciences*, Mack Publishing Company, a standard reference text in this field.

Useful pharmaceutical dosage forms for administration of the compounds of this invention can be illustrated as follows.

Capsules: Capsules are prepared by filling standard two-piece hard gelatin capsulates each with 100 milligrams of powdered active ingredient, 175 milligrams of lactose, 24 milligrams of talc and 6 milligrams magnesium stearate.

Soft Gelatin Capsules: A mixture of active ingredient in soybean oil is prepared and injected by means of a positive displacement pump into gelatin to form soft gelatin capsules containing 100 milligrams of the active ingredient. The capsules are then washed and dried.

Tablets: Tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or to delay absorption.

Injectable: A parenteral composition suitable for administration by injection is prepared by stirring 1.5% by weight of active ingredients in 10% by volume propylene glycol and water. The solution is made isotonic with sodium chloride and sterilized.

Suspension: An aqueous suspension is prepared for oral administration so that each 5 millimeters contain 100 milligrams of finely divided active ingredient, 200 milligrams of sodium carboxymethyl cellulose, 5 milligrams of sodium benzoate, 1.0 grams of sorbitol solution U.S.P. and 0.025 millimeters of vanillin.

In the present disclosure it should be understood that the specified materials and conditions are important in practicing the invention but that unspecified materials and conditions are not excluded so long as they do not prevent the benefits of the invention from being realized.

What is claimed:

1. A compound of the formula:

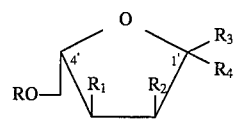

or a pharmaceutically acceptable salt thereof, wherein

R is H, $COR_5$, $P(O)_nR_6R_7$, or $SO_3H$ wherein $R_5$ is alkyl of 1–5 carbon atoms or an aromatic ring structure, $R_6$ and $R_7$ are each H or alkyl of 1–5 carbon atoms and n is 2 or 3;

$R_1$ and $R_2$ are independently H, mono- or di-halogen, or $OR_8$ wherein $R_8$ is H, $COR_9$, $P(O)_mR_{10}R_{11}$ wherein $R_9$ is $H_2$, substituted or unsubstituted alkyl of 1–5 carbon atoms or a substituted or unsubstituted aromatic ring structure, $R_{10}$ and $R_{11}$ are each H or alkyl of 1–5 carbon atoms and m is 2 or 3, provided that when $R_2$ is OH, $R_2$ and B can combine to form a 5- membered cyclic ring structure;

$R_3$ and $R_4$ are independently B, H or $OR_{12}$ where $R_{12}$ is H, $COR_{13}$, $P(O)_pR_{14}R_{15}$ wherein $R_{13}$ is substituted or unsubstituted alkyl of 1–5 carbon atoms or a substituted or unsubstituted aromatic ring structure, $R_{14}$ and $R_{15}$ are each H or alkyl of C1-C5 carbon atoms and p is 2 or 3;

B is a naturally-occurring nucleobase selected from the group consisting of A, G, C, U, hypoxanthine or T or a modified base comprising one or more substitutions selected from the group consisting of H, halogen, C1-C6 alkyl, C2-C6 alkenyl, C1-C6 alkoxy, C3-C6 cycloalkyl-C1-C6 alkoxy, C3-C8 cycloalkyloxy, C3-C8 cycloalkylthio, C1-C6 alkylthio, a substituted amino group, an aryl, aralkyl, aryloxy, aralkoxy, arylthio, aralkylthio, a heterocyclic ring and an amino group, provided that when the base is a pyrimidine, the atom at position 4 of the base can be sulfur and further provided that when the base is a purine, the atom at position 6 of the base may be sulfur, provided that:

only one of $R_3$ or $R_4$ can be B and there is only one B;

when R=H, $R_1$=OH, $R_2$=H, $R_3$=H and $R_4$=B, then B cannot be U, C, T, 5-FU, hypoxanthine, A or G;

when R=H, $R_1$=OH, $R_2$=OH, $R_3$=B and $R_4$=H, then B cannot be C;

when R=H, $R_1$=OH, $R_2$=OH, $R_3$=H and $R_4$=B, then B cannot be 5-FU, C, U, A or hypoxanthine;

when R=H, $R_1$=OH, $R_2$=H, $R_3$=B and $R_4$=H, then B cannot be 5-FU, A, C, G, T, U or hypoxanthine;

when R=H, $R_1$=H, $R_2$=H, $R_3$=B and $R_4$=H, then B cannot be A, C, G, T, U, 5-FU, or hypoxanthine;

when R=H, $R_1$=H, $R_2$=H, $R_3$=H and $R_4$=B, then B can not be A, C, G, T, U, 5-FU or hypoxanthine;

when R=H or $P(O)_mR_{10}R_{11}$, where $R_{10}$=H and $R_{11}$=H and m=3, and $R_1$ and $R_2$ are independently H or F; and $R_3$=H and $R_4$=B, then B cannot be U, C, T, A, G or hypoxanthine; and when R=H or $P(O)_mR_{10}R_{11}$, where $R_{10}$=H, $R_{11}$=H, and m=3; and $R_1$ and $R_2$ are independently H or F; and $R_3$=B and $R_4$=H, then B cannot be U, C, T, A, G or hypoxanthine.

2. A compound of claim 1 wherein $R_3$ is defined as B and $R_4$ is H.

3. A compound of claim 1 wherein $R_4$ is defined as B and $R_3$ is H.

4. A compound of claim 1 wherein B is a nucleobase selected from the group consisting of C, T, U, G, A, hypoxanthine, 6-thioguanine, 4-thiouracil and 5-fluorouracil.

5. A compound of claim 1 wherein R is H.

6. A compound of claim 1 wherein $R_1$ and $R_2$ are each independently H or OH.

7. A compound of claim 6 wherein $R_2$ is OH and combines with B to form a 5-membered cyclic ring.

8. A compound of claim 1 wherein $R_3$ is B; B is a nucleobase selected from the group consisting of C, T, U, G, A, hypoxanthine, 6-thioguanine, 4-thiouracil and 5-fluorouracil; R is H; $R_1$ and $R_2$ are each independently H or OH; and $R_4$=H.

9. A compound of claim 1 wherein $R_4$ is B; B is a nucleobase selected from the group consisting of C, T, U, G, A, hypoxanthine, 6-thioguanine, 4-thiouracil and 5-fluorouracil; R is H; $R_1$ and $R_2$ are each independently H or OH; and $R_3$=H.

10. An anhydride derivative of a compound of claim 1, selected from the group consisting of 2-amino-α-L-ribofurano [1',2':4,5]oxazoline, and $O^{2,2'}$-anhydro-1-a-L-ribofurano syluracil.

11. The compound of claim 1 which is selected from the group consisting of α-L-ribofuranosyluracil; 1-(2,3,5-tri-O-benzoyl-α-L-ribofuranosyl)-4-thiouracil; α-L-ribofuranosyl-4thiouracil; 1-(3,5-di-O-benzoyl-2-deoxy-β-L-ribofuranosyl)-4-thiouracil; 2'-β-L-deoxyribofuranosyl-4-thiouracil; α-L-ribofuranosyl-5-fluorouracil; β-L-ribofuranosylguanine; β-L-ribofuranosyl-6-thioguanine; or a pharmaceutically acceptable salt thereof.

12. A pharmaceutical composition comprising a pharmaceutically acceptable carrier and a therapeutically effective amount of one or more of the compounds of claim 1.

13. A pharmaceutical composition comprising a pharmaceutically acceptable carrier and a therapeutically effective amount of one or more of the compounds of claim 11.

* * * * *